(12) United States Patent
Lazarus et al.

(10) Patent No.: US 8,476,023 B2
(45) Date of Patent: Jul. 2, 2013

(54) METHODS RELATING TO AROMATASE INHIBITOR PHARMACOGENETICS

(75) Inventors: Philip Lazarus, Hummelstown, PA (US); Dongxiao Sun, Hummelstown, PA (US)

(73) Assignee: The Penn State Research Foundation, University Park, PA (US)

( * ) Notice: Subject to any disclaimer, the term of this patent is extended or adjusted under 35 U.S.C. 154(b) by 314 days.

(21) Appl. No.: 12/852,957

(22) Filed: Aug. 9, 2010

(65) Prior Publication Data

US 2011/0033856 A1    Feb. 10, 2011

Related U.S. Application Data

(60) Provisional application No. 61/232,160, filed on Aug. 7, 2009.

(51) Int. Cl.
*C12Q 1/68* (2006.01)
*C12N 15/54* (2006.01)
*C12N 15/52* (2006.01)

(52) U.S. Cl.
USPC ......... 435/6.18; 435/6.11; 435/6.13; 435/7.1; 536/23.2

(58) Field of Classification Search
None
See application file for complete search history.

(56) References Cited

U.S. PATENT DOCUMENTS

2007/0172844 A1    7/2007    Lancaster et al.
2007/0172853 A1    7/2007    McCarroll et al.
2009/0023149 A1    1/2009    Knudsen

OTHER PUBLICATIONS

Ahern, The Scientist 9 (15), 20 (1995).*
Ariazi E. et al., Exemestane's 17-hydroxylated metabolite exerts biological effects as an androgen, *Mol Cancer Ther*, 6: 2817-2827, 2007.
Balliet, R. et al., Characterization of UGTs active against SAHA and association between SAHA glucuronidation activity phenotype with UGT genotype, *Cancer Research*, 69(7): 2981-89, 2009.
Buzzetti, F. et al., Synthesis and aromatase inhibition by potential metabolites of exemestane (6-methylenandrosta-1,4-diene-3,17-dione). *Steroids*, 58(11):527-532, 1993.
Corona G. et al., A liquid chromatography-tandem mass spectrometry method for the simultaneous determination of exemestane and its metabolite 17-dihydroexemestane in human plasma, *J Mass Spectrom*; 44: 920-928, 2009.
Desai, A. et al., UGT Pharmacogenomics: Implications for Cancer Risk and Cancer Therapeutics, *Pharmacogenomics*, 13: 517-523, 2003.
Evans T. et al., Phase I and endocrine study of exemestane (FCE 24304), a new aromatase inhibitor, in postmenopausal women, *Cancer Res*; 52:5933-5939, 1992.

Fuerst, M., Searching for Predictors of Exemestane Activity: Small Study is Start, *Oncology Times*, 26(18): Sep. 25, 2004, p. 21.
Gallagher, et al., The UGT2B17 gene deletion polymorphism and risk of prostate cancer. A case-control study in Caucasians, Cancer Detection Prevention, 31(4): 310-15, 2007.
Gallagher, C. et al., The UDP-glucuronosyltransferase 2B17 gene deletion polymorphism: sex-specific association with urinary 4-(methylnitrosamino)-1-(3-pyridyl)-1-butanol glucuronidation phenotype and risk for lung cancer, *Cancer Epidemiology, Biomarkers and Preventions*, 16(4): 823-28, Apr. 2007.
Juul, A. et al., A Common Deletion in the Uridine Diphosphate Glucuronyltransferase (UGT) 2B17 Gene is a Strong Determinant of Androgen Excretion in Healthy Pubertal Boys, *The Journal of Clinical Endocrinology and Metabolism*, 94(3): 1005-1011, Mar. 2009 (Abstract only).
Lazarus, P. et al., Genotype-Phenotype Correlation Between the Polymorphic UGT2B17 Gene Deletion and NNAL Glucuronidation Activities in Human Liver Microsomes, *Pharmacogenetics and Genomics*, 15(11): 769-778, Nov. 2005.
Mareck, J. et al., Identification of the aromatase inhibitors anastrozole and exemestane in human urine using liquid chromatography/tandem mass spectrometry, *Rapid Communications in Mass Spectrometry*, 20(12): 1954-62, 2006.
Markopoulos, C. et al., The effect of exemestane on the lipidemic profile of postmenopausal early breast cancer patients: preliminary results of the TEAM Greek sub-study. *Breast Cancer Res Treat*, 93(1):61-66, 2005.
Nagar, S. et al., Uridine Diphosphoglucuronosyltransferase Pharmacogenetics and Cancer, *Oncogene*, 25: 1659-1672, 2006.
Park, J. et al., Deletion Polymorphism of UDP-Glucuronosyltransferase 2B17 and Risk of Prostate Cancer in African American and Caucasian Men, *Cancer Epidemiology, Biomarkers & Prevention*, 15(8): 1473-1478, Aug. 2006 (Abstract only).
Schulze, J. et al., Doping test results dependent on genotype or uridine diphosphoglucuronosyl transferase 2B17, the major enzyme for testosterone glucuronidation, *Journal of Clinical Endocrinology and Metabolism*, 93(7): 2500-06, Mar. 2008 (Abstract only).
Sun D. et al., Characterization of 17-dihydroexemestane glucuronidation: potential role of the UGT2B17 deletion in exemestane pharmacogenetics, *Pharmacogenet Genomics*, 20(10):575-85, 2010.
Swanson, C. et al., The Uridine Diphosphate Glucuronosyltransferase 2B15 D85Y and 2B17 Deletion Polymorphisms Predict the Glucuronidation Pattern of Androgens and Fat Mass in Men, *The Journal of Clinical Endocrinology and Metabolism*, 92(12): 4878-4892, Dec. 2007 (Abstract only).
Traina T. et al., Pharmacokinetics and tolerability of exemestane in combination with raloxifene in postmenopausal women with a history of breast cancer, Breast Cancer Res Treat; 111:377-388, 2008.

* cited by examiner

*Primary Examiner* — James Martinell
(74) *Attorney, Agent, or Firm* — Gifford, Krass, Sprinkle, Anderson & Citkowski, P.C.

(57) ABSTRACT

Methods for aiding in determining therapeutic efficacy of an aromatase inhibitor in a subject are provided according to embodiments of the present invention which include detecting expression and/or function of at least one UDP-glucuronosyltransferase having activity to modify at least one aromatase inhibitor and/or metabolite of the aromatase inhibitor by glucuronidation, wherein detection of expression and/or function of the UDP-glucuronosyltransferase is correlated with therapeutic efficacy of the aromatase inhibitor in the subject. Detection of UDP-glucuronosyltransferase expression and/or function includes detection of a UDP-glucuronosyltransferase gene deletion polymorphism in the subject.

18 Claims, 9 Drawing Sheets

SEQUENCE LISTING

```
<160> NUMBER OF SEQ ID NOS: 11

<210> SEQ ID NO 1
<211> LENGTH: 30
<212> TYPE: DNA
<213> ORGANISM: artificial
<220> FEATURE:
<223> OTHER INFORMATION: primer for amplification of a portion of
      UGT2B17 gene including exon 1

<400> SEQUENCE: 1
tgaaaatgtt cgatagatgg acatatagta                                    30

<210> SEQ ID NO 2
<211> LENGTH: 29
<212> TYPE: DNA
<213> ORGANISM: artificial
<220> FEATURE:
<223> OTHER INFORMATION: primer for amplification of a portion of
      UGT2B17 gene including exon 1

<400> SEQUENCE: 2
gacatcaaat tttgactctt gtagttttc                                     29

<210> SEQ ID NO 3
<211> LENGTH: 38
<212> TYPE: DNA
<213> ORGANISM: artificial
<220> FEATURE:
<223> OTHER INFORMATION: UGT2B17 probe

<400> SEQUENCE: 3
tacattttgg tcatattttt cacaactaca agaattgt                           38

<210> SEQ ID NO 4
<211> LENGTH: 25
<212> TYPE: DNA
<213> ORGANISM: artificial
<220> FEATURE:
<223> OTHER INFORMATION: primer flanking a deletion mutation
      polymorphism of  UGT2B17 gene

<400> SEQUENCE: 4
```

```
tttaatgttt tctgccttat gccac                                           25
```

<210> SEQ ID NO 5
<211> LENGTH: 27
<212> TYPE: DNA
<213> ORGANISM: artificial
<220> FEATURE:
<223> OTHER INFORMATION: primer flanking a deletion mutation
      polymorphism of UGT2B17 gene

<400> SEQUENCE: 5

```
agcctatgca attttcattc aacatag                                         27
```

<210> SEQ ID NO 6
<211> LENGTH: 40
<212> TYPE: DNA
<213> ORGANISM: artificial
<220> FEATURE:
<223> OTHER INFORMATION: UGT2B17 probe

<400> SEQUENCE: 6

```
actacactga gatttacaaa agaattctgt caggatatag                           40
```

<210> SEQ ID NO 7
<211> LENGTH: 530
<212> TYPE: PRT
<213> ORGANISM: Homo sapiens

<400> SEQUENCE: 7

```
Met Ser Leu Lys Trp Met Ser Val Phe Leu Leu Met Gln Leu Ser Cys
1               5                   10                  15

Tyr Phe Ser Ser Gly Ser Cys Gly Lys Val Leu Val Trp Pro Thr Glu
            20                  25                  30

Tyr Ser His Trp Ile Asn Met Lys Thr Ile Leu Glu Glu Leu Val Gln
        35                  40                  45

Arg Gly His Glu Val Ile Val Leu Thr Ser Ser Ala Ser Ile Leu Val
    50                  55                  60

Asn Ala Ser Lys Ser Ser Ala Ile Lys Leu Glu Val Tyr Pro Thr Ser
65                  70                  75                  80

Leu Thr Lys Asn Asp Leu Glu Asp Phe Phe Met Lys Met Phe Asp Arg
                85                  90                  95

Trp Thr Tyr Ser Ile Ser Lys Asn Thr Phe Trp Ser Tyr Phe Ser Gln
            100                 105                 110

Leu Gln Glu Leu Cys Trp Glu Tyr Ser Asp Tyr Asn Ile Lys Leu Cys
        115                 120                 125

Glu Asp Ala Val Leu Asn Lys Lys Leu Met Arg Lys Leu Gln Glu Ser
    130                 135                 140

Lys Phe Asp Val Leu Leu Ala Asp Ala Val Asn Pro Cys Gly Glu Leu
145                 150                 155                 160

Leu Ala Glu Leu Leu Asn Ile Pro Phe Leu Tyr Ser Leu Arg Phe Ser
                165                 170                 175

Val Gly Tyr Thr Val Glu Lys Asn Gly Gly Phe Leu Phe Pro Pro
            180                 185                 190

Ser Tyr Val Pro Val Val Met Ser Glu Leu Ser Asp Gln Met Ile Phe
        195                 200                 205

Met Glu Arg Ile Lys Asn Met Ile Tyr Met Leu Tyr Phe Asp Phe Trp
    210                 215                 220

Phe Gln Ala Tyr Asp Leu Lys Lys Trp Asp Gln Phe Tyr Ser Glu Val
225                 230                 235                 240
```

Leu Gly Arg Pro Thr Thr Leu Phe Glu Thr Met Gly Lys Ala Glu Met
            245                 250                 255

Trp Leu Ile Arg Thr Tyr Trp Asp Phe Glu Phe Pro Arg Pro Phe Leu
            260                 265                 270

Pro Asn Val Asp Phe Val Gly Gly Leu His Cys Lys Pro Ala Lys Pro
            275                 280                 285

Leu Pro Lys Glu Met Glu Glu Phe Val Gln Ser Ser Gly Glu Asn Gly
            290                 295                 300

Ile Val Val Phe Ser Leu Gly Ser Met Ile Ser Asn Met Ser Glu Glu
305                 310                 315                 320

Ser Ala Asn Met Ile Ala Ser Ala Leu Ala Gln Ile Pro Gln Lys Val
                    325                 330                 335

Leu Trp Arg Phe Asp Gly Lys Lys Pro Asn Thr Leu Gly Ser Asn Thr
            340                 345                 350

Arg Leu Tyr Lys Trp Leu Pro Gln Asn Asp Leu Leu Gly His Pro Lys
            355                 360                 365

Thr Lys Ala Phe Ile Thr His Gly Gly Thr Asn Gly Ile Tyr Glu Ala
            370                 375                 380

Ile Tyr His Gly Ile Pro Met Val Gly Ile Pro Leu Phe Ala Asp Gln
385                 390                 395                 400

His Asp Asn Ile Ala His Met Lys Ala Lys Gly Ala Ala Leu Ser Val
                    405                 410                 415

Asp Ile Arg Thr Met Ser Ser Arg Asp Leu Leu Asn Ala Leu Lys Ser
            420                 425                 430

Val Ile Asn Asp Pro Ile Tyr Lys Glu Asn Ile Met Lys Leu Ser Arg
            435                 440                 445

Ile His His Asp Gln Pro Val Lys Pro Leu Asp Arg Ala Val Phe Trp
            450                 455                 460

Ile Glu Phe Val Met Arg His Lys Gly Ala Lys His Leu Arg Val Ala
465                 470                 475                 480

Ala His Asn Leu Thr Trp Ile Gln Tyr His Ser Leu Asp Val Ile Ala
                    485                 490                 495

Phe Leu Leu Ala Cys Val Ala Thr Met Ile Phe Met Ile Thr Lys Cys
            500                 505                 510

Cys Leu Phe Cys Phe Arg Lys Leu Ala Lys Thr Gly Lys Lys Lys Lys
            515                 520                 525

Arg Asp
    530

<210> SEQ ID NO 8
<211> LENGTH: 1593
<212> TYPE: DNA
<213> ORGANISM: Homo sapiens

<400> SEQUENCE: 8
atgtctctga aatggatgtc agtctttctg ctgatgcagc tcagttgtta ctttagctct      60
gggagttgtg aaaggtgct ggtgtggccc acagaataca gccattggat aaatatgaag     120
acaatcctgg aagagcttgt tcagaggggt catgaggtga ttgtgttgac atcttcggct     180
tctattcttg tcaatgccag taaatcatct gctattaaat agaagtttta tcctacatct     240
ttaactaaaa atgatttgga agatttttt atgaaaatgt tcgatagatg gacatatagt      300
atttcaaaaa atacattttg gtcatatttt tcacaactac aagaattgtg ttgggaatat     360
tctgactata atataaagct ctgtgaagat gcagttttga caagaaact tatgagaaaa      420

```
ctacaagagt caaaatttga tgtccttctg gcagatgccg ttaatccctg tggtgagctg      480
ctggctgagc tacttaacat acccttctg tacagtctcc gcttctctgt tggctacaca       540
gttgagaaga atggtggagg atttctgttc cctccttcct atgtacctgt tgttatgtca      600
gaattaagtg atcaaatgat tttcatggag aggataaaaa atatgatata tatgctttat      660
tttgactttt ggtttcaagc atatgatctg aagaagtggg accagttta tagtgaagtt      720 ctaggaagac ccactacatt atttgagaca atggggaaag ctgaaatgtg gctcattcga      780
acctattggg attttgaatt tcctcgccca ttcttaccaa atgttgattt tgttggagga      840
cttcactgta aaccagccaa acccttgcct aaggaaatgg aagagtttgt gcagagctct      900
ggagaaaatg gtattgtggt gttttctctg gggtcgatga tcagtaacat gtcagaagaa      960
agtgccaaca tgattgcatc agcccttgcc cagatcccac aaaaggttct atggagattt      1020
gatggcaaga agccaaatac tttaggttcc aatactcgac tgtataagtg gttaccccag      1080
aatgaccttc ttggtcatcc caaaaccaaa gcttttataa ctcatggtgg aaccaatggc      1140
atctatgagg caatctacca tgggatccct atggtgggca ttcccttgtt tgcggatcaa      1200
catgataaca ttgctcacat gaaagccaag ggagcagccc tcagtgtgga catcaggacc      1260
atgtcaagta gagatttgct caatgcattg aagtcagtca ttaatgaccc tatctataaa      1320
gagaatatca tgaaattatc aagaattcat catgatcaac cggtgaagcc cctggatcga      1380
gcagtcttct ggattgagtt tgtcatgcgc cataaaggag ccaagcacct tcgggtcgca      1440
gcccacaacc tcacctggat ccagtaccac tctttggatg tgatagcatt cctgctggcc      1500
tgcgtggcaa ctatgatatt tatgatcaca aaatgttgcc tgttttgttt ccgaaagctt      1560
gccaaaacag gaaagaagaa gaaaagggat tag                                   1593
```

<210> SEQ ID NO 9
<211> LENGTH: 23
<212> TYPE: DNA
<213> ORGANISM: Artificial Sequence
<220> FEATURE:
<223> OTHER INFORMATION: aromatase sense primer

<400> SEQUENCE: 9
ccagacgtcg cgactctaaa ttg                                              23

<210> SEQ ID NO 10
<211> LENGTH: 22
<212> TYPE: DNA
<213> ORGANISM: Artificial Sequence
<220> FEATURE:
<223> OTHER INFORMATION: aromatase antisense primer

<400> SEQUENCE: 10
ctgtgaggat gacactattg gc                                               22

<210> SEQ ID NO 11
<211> LENGTH: 17
<212> TYPE: PRT
<213> ORGANISM: Artificial Sequence
<220> FEATURE:
<223> OTHER INFORMATION: UGT2B peptide

<400> SEQUENCE: 11

Cys Lys Trp Asp Gln Phe Tyr Ser Glu Val Leu Gly Arg Pro Thr Thr
1               5                   10                  15

Leu

METHODS RELATING TO AROMATASE INHIBITOR PHARMACOGENETICS

REFERENCE TO RELATED APPLICATION

This application claims priority to U.S. Provisional Patent Application Ser. No. 61/232,160, filed Aug. 7, 2009, the entire content of which is incorporated herein by reference.

GOVERNMENT SUPPORT

This invention was made with government support under RO1-DE13158 awarded by the National Institutes of Health. The government has certain rights in the invention.

FIELD OF THE INVENTION

Embodiments of the present invention provide methods relating to aromatase inhibitor pharmacogenetics in a subject.

BACKGROUND OF THE INVENTION

Aromatases are enzymes that synthesize estrogen from androgens, and aromatase inhibitors block this conversion. This lowers the estrogen level in a person treated with an aromatase inhibitor, slowing the growth of estrogen-responsive cancers, such as breast cancer and ovarian cancer, or providing other benefits of decreased androgen conversion to estrogen. Examples of aromatase inhibitors include exemestane, anastrozole, letrozole, vorozole, formestane and fadrozole.

Numerous therapeutic choices are available to clinicians for treatment of estrogen-responsive cancers and in other conditions where it is desirable to decrease estrogen produced in a subject. However, because of the expense and inconvenience to the subject of treatment with a drug which is ineffective in the subject, it is desirable to determine which drugs are or will be therapeutically effective in the subject.

Embodiments of the present invention provide methods for aiding in determining the therapeutic efficacy of an aromatase inhibitor in a subject.

SUMMARY OF THE INVENTION

Methods for aiding in determining therapeutic efficacy of exesmestane in a subject are provided according to embodiments of the present invention which include assaying a biological sample obtained from the subject for a UDP glucuronosyltransferase 2 family, polypeptide B17, UGT2B17, gene deletion polymorphism. It is an aspect of the present invention that detection of the UDP glucuronosyltransferase 2 family, polypeptide B17 gene deletion polymorphism is correlated with altered therapeutic efficacy of the exesmestane in the subject. Assaying a UGT2B17 gene deletion polymorphism is performed using polymerase chain reaction according to embodiments of the present invention. Optionally, the polymerase chain reaction is a real-time polymerase chain reaction.

Methods for aiding in determining therapeutic efficacy of exesmestane in a human subject are provided according to embodiments of the present invention which include assaying a biological sample obtained from the human subject for a UDP glucuronosyltransferase 2 family, polypeptide B17, UGT2B17, gene deletion polymorphism.

According to embodiments of the present invention, the biological sample assayed includes genomic DNA.

According to embodiments of the present invention methods for aiding in determining therapeutic efficacy of exesmestane in a subject include assaying a biological sample obtained from the subject for a UGT2B17 gene deletion polymorphism by hybridization of nucleic acids in the biological sample with a probe specific for a UGT2B17 nucleic acid under suitable hybridization conditions, and detection of hybridization of the probe and the UGT2B17 nucleic acid, wherein a lack of detectable hybridization of the probe and the UGT2B17 nucleic acid is indicative of a UGT2B17 gene deletion polymorphism. According to embodiments of the present invention, the probe hybridizes under high stringency conditions to SEQ ID No. 8, or a portion thereof specific to UGT2B17. According to embodiments of the present invention, the probe hybridizes under high stringency conditions to a nucleic acid encoding SEQ ID No. 7 or a portion thereof specific to UGT2B17. The term "specific to UGT2B17" refers to a portion of the indicated amino acid or nucleic acid sequence that identifies the amino acid or nucleic acid sequence as a UGT2B17 amino acid or nucleic acid sequence and distinguishes it from amino acids or nucleic acid sequences of other genes.

The term "probe" refers to a nucleic acid sequence capable of hybridizing with a UGT2B17 nucleic acid, such as genomic DNA, cDNA, a transcript of genomic DNA or cDNA, or the complement thereof, to form a hybridization complex of the probe and UGT2B17 nucleic acid. A probe is optionally labeled with a detectable label to detect the hybridization complex of the probe and UGT2B17 nucleic acid.

Kits for aiding in determining therapeutic efficacy of exemestane in a subject are provided according to embodiments of the present invention which include at least one reagent for detection of a UGT2B17 gene deletion polymorphism. For example, kits are provided including one or more primers or probes for detection of a UGT2B17 gene deletion polymorphism. The term "primer" refers to an oligonucleotide capable of acting as a point of initiation for synthesis of a primer extension product complementary to a template nucleic acid. Examples of primers and probes for detection of a UGT2B17 gene deletion polymorphism include, but are not limited to, SEQ ID Nos. 1, 2, 3, 4, 5 and 6.

Kits for aiding in determining therapeutic efficacy of exemestane in a subject are provided according to embodiments of the present invention which include at least one probe or primer selected from SEQ ID Nos. 1, 2, 3, 4, 5 and 6.

Methods of detecting exemestane use in a subject are provided according to embodiments of the present invention which include assaying a biological sample obtained from the subject for a UGT2B17 gene deletion polymorphism. The terms "exemestane use" and "using exemestane" refer to introduction of exemestane into the body of a subject including, but not limited to, introduction of exemestane into the body of a subject by ingestion or injection. Detection of a UGT2B17 gene deletion polymorphism is found according to aspects of the present invention to be correlated with decreased production of glucuronidated 17-dihydroexemestane in the urine of a subject who is using exemestane compared to a control subject who has no UGT2B17 gene deletion polymorphism and is using exemestane.

Detecting no UGT2B17 gene deletion polymorphism supports a finding of no exemestane use in the subject when glucuronidated 17-dihydroexemestane is not detected in urine. Methods of the present invention optionally further include assaying a urine sample obtained from a subject for glucuronidated 17-dihydroexemestane.

Methods of detecting exesmestane use in a subject optionally further include assaying a blood sample obtained from the subject for exemestane.

Methods for aiding in determining therapeutic efficacy of an aromatase inhibitor in a subject are provided according to embodiments of the present invention which include detecting expression and/or function of at least one UDP-glucuronosyltransferase having activity to modify at least one aromatase inhibitor and/or metabolite of the aromatase inhibitor by glucuronidation, wherein detection of expression and/or function of the UDP-glucuronosyltransferase is correlated with therapeutic efficacy of the aromatase inhibitor in the subject. Detection of UDP-glucuronosyltransferase expression and/or function includes detection of a UDP-glucuronosyltransferase gene deletion polymorphism in the subject Methods for aiding in determining therapeutic efficacy of an exemestane in a subject are provided according to embodiments of the present invention which include detecting expression and/or function of UGT2B17. Altered expression and/or function of UGT2B17 compared to control subjects is found to result in altered therapeutic efficacy of exemestane in subjects having altered expression and/or function of UGT2B17.

DETAILED DESCRIPTION OF THE INVENTION

Figure 1:
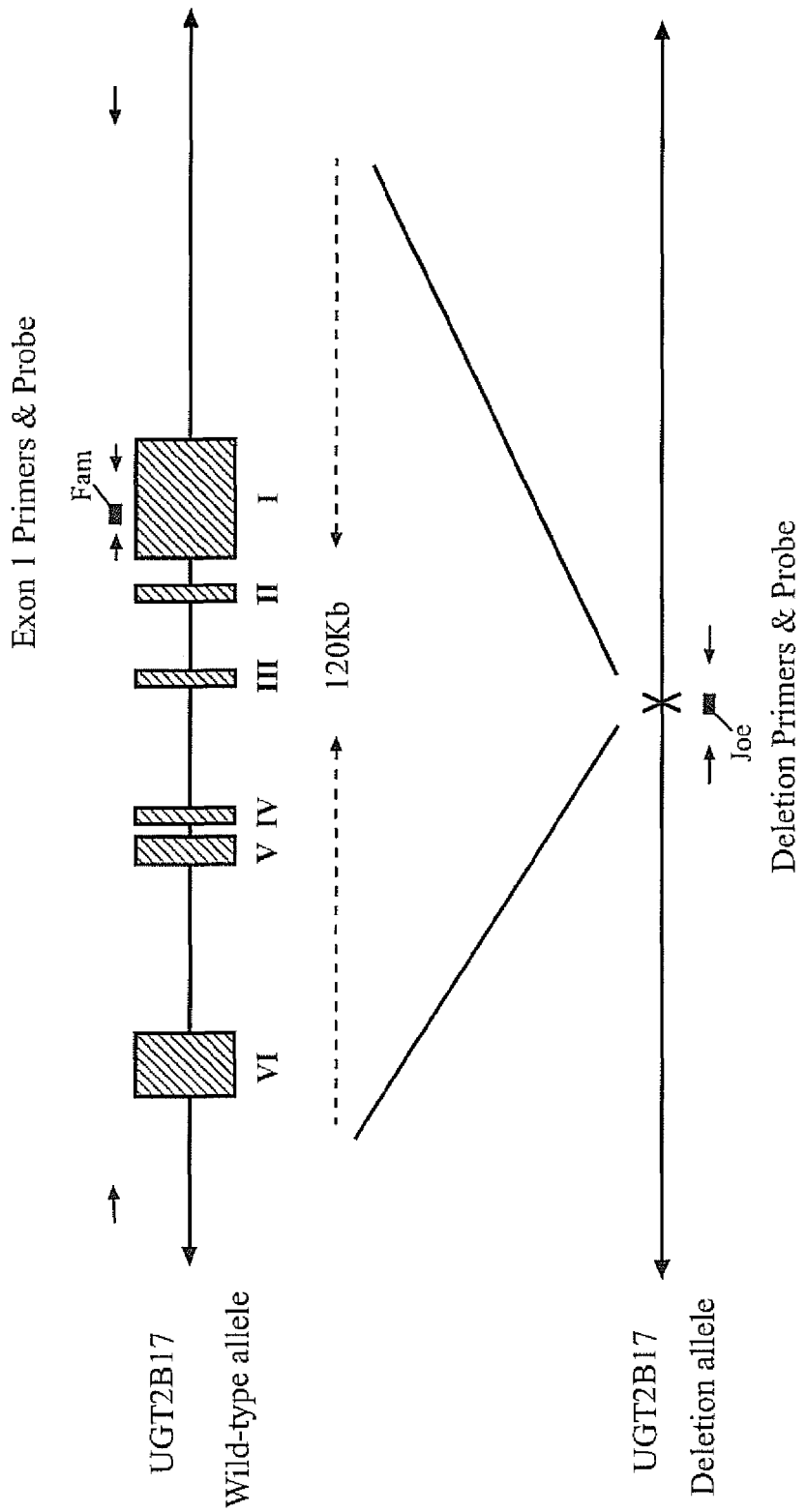
FIG. 1 shows gene structure and primer and probe locations for a UGT2B17 multiplex real-time PCR assay.
Figure 2:
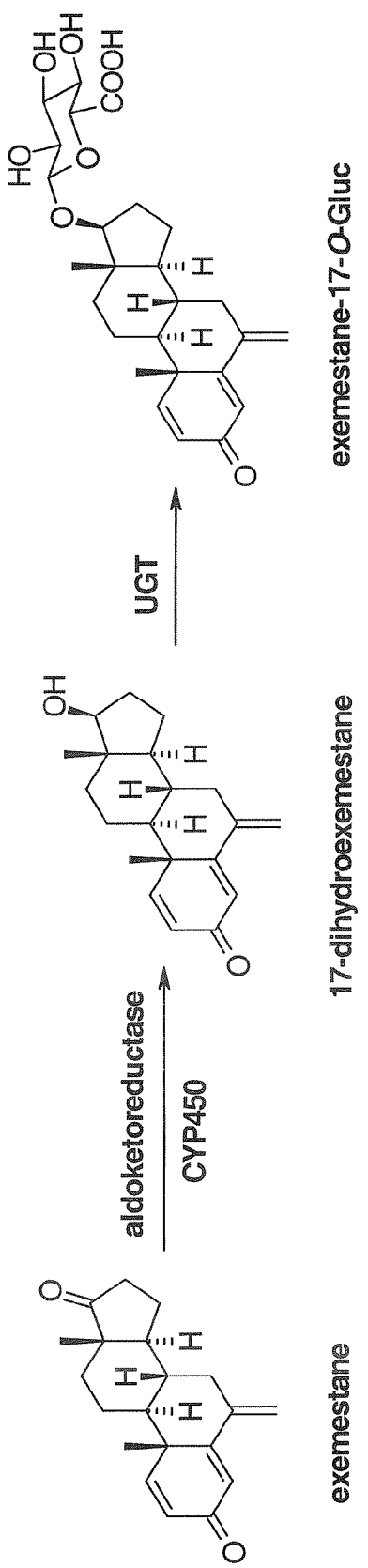
FIG. 2 is a schematic drawing of exesmestane metabolism.

Aspects of the present invention include methods, compositions and kits for aiding in determining therapeutic efficacy of an aromatase inhibitor treatment in a subject. In particular embodiments, methods, compositions and kits are provided by the present invention for aiding determining therapeutic efficacy of exemestane treatment in a subject.

Aromatase enzymes convert androgens, such as testosterone and androstendione into estrogenic steroid hormones and aromatase inhibitors are agents which inhibit aromatase enzymes.

Exemestane is a well-known aromatase inhibitor, known commercially as Aromasin®, and chemically described as 6-methylenandrosta-1,4-diene-3,17-dione. Exemestane is used clinically to treat estrogenic steroid hormone-responsive malignancies by reducing production of estrogens, such as estrone and estradiol. Exemestane is also used by individuals, such as body builders and atheletes, to inhibit production of estrogens from androgens.

The term "therapeutic efficacy" is used to refer to the therapeutic effect of a drug or candidate drug in a subject. Therapeutic effects of aromatase inhibitors, including exemestane include significant reduction of circulating estrogen levels in a subject. In individuals having estrogen-responsive malignancies, therapeutic effects of aromatase inhibitors include reduction of one or more signs and/or symptoms of cancer in a subject. Therapeutic efficacy of exemestane can be measured, for example, by monitoring estrogen levels and/or reduction in tumor size using standard medical methodology in a subject.

It is an aspect of the present invention that UDP glucuronosyltransferase 2 family, polypeptide B17 (UGT2B17) is found to have activity to modify at least one metabolite of exemestane by glucuronidation, particularly 17-dihydroexemestane. It is a further aspect of the present invention that individuals having increased or decreased glucuronidation of at least one metabolite of exemestane, particularly 17-dihydroexemestane, by UGT2B17 have correspondingly decreased or increased therapeutic efficacy of exemestane treatment and determination of UGT2B17 gene deletion, mRNA and/or protein expression and/or enzyme activity in an individual subject therefore aids in determination of therapeutic efficacy of exemestane treatment in the individual.

UGT2B17 is a well-known UDP glucuronosyltransferase, see for example, Beaulieu et al., J. Biol Chem., 271:22855-22862, 1996; Gallagher et al, Cancer Detect. Prev., 31:310-315, 2007; Murata et al, J. Exp. Med., 197:1279-1289, 2003; Lazarus et al, Pharmacogenet. Genomics, 15:769-778, 2005; Park et al, Cancer Epidemiol. Biomarkers Prev., 15:1473-1478, 2006; McCarroll et al, Nature Genet., 38:86-92, 2006; and Wilson et al, Genomics, 84:717-714, 2004.

A human UGT2B17 amino acid sequence is shown herein as SEQ ID No. 7 and a nucleic acid sequence encoding the UGT2B17 protein of SEQ ID No. 7 is shown herein as SEQ ID No. 8. In humans the UGT2B17 gene is on chromosome: 4; location: 4q13; having NCBI annotation: chromosome 4, NC_000004.11, 69402902 . . . 69434245, complement.

Methods provided according to embodiments of the present invention include detection of a UGT2B17 deletion mutation, detection of increased or decreased UGT2B17 expression and/or detection of increased or decreased UGT2B17 activity, in a biological sample.

Methods described herein have utility to aid in determining therapeutic efficacy of exemestane treatment in a subject as well as to aid in detection of exemestane use by a subject.

Embodiments of the present invention include detecting the presence or absence of a UGT2B17 deletion mutation in a biological sample using methods for detection of a UGT2B17 gene deletion mutation and/or methods for detection of UGT2B17 nucleic acids and/or UGT2B17 protein encoded by the UGT2B17 gene.

A biological sample assayed according to methods of the present invention is obtained from a subject.

The biological sample is any substance containing or presumed to contain UGT2B17 nucleic acids or protein such as cells, tissues and fluids including, but not limited to, saliva; blood; semen; mucosal swab, such as buccal swab or nasal swab; hair; tears; stool; secretions of the skin, genitorurinary tract, respiratory tract, intestinal tract; biopsy material, particularly liver biopsy material; and sample of isolated nucleic acids, such as genomic DNA, cDNA and mRNA.

Embodiments of methods of the present invention are described herein with particular reference to samples obtained from a subject, however, such methods are not limited to analysis of samples obtained directly from a subject. For example, genomic DNA template can be obtained from cultured cells, including, but not limited to, cultured cells derived from a human such as cell lines, primary cells or laboratory manipulated cells such as recombinant cells.

A sample from a subject is optionally purified for assay according to a method of the present invention. The term "purified" in the context of a sample refers to separation of a biomarker from at least one other component present in the sample. Sample purification is achieved by techniques illustratively including electrophoretic methods such as gel electrophoresis and 2-D gel electrophoresis; chromatography methods such as HPLC, ion exchange chromatography, affinity chromatography, size exclusion chromatography, thin layer and paper chromatography.

One or more standards can be used to allow quantitative determination of UGT2B17 protein or nucleic acid, in a sample.

The term "subject" as used herein refers particularly to human subjects, although compositions and methods of the present invention are applicable to subjects of other species, such as non-human primates, other mammals, birds, reptiles, insects and microorganisms. A subject is preferably a mammal, such as non-human primate, cat, dog, sheep, cow, goat, horse, pig, poultry, bird, rabbit and rodent. In preferred embodiments, the subject is human.

Detection of a UGT2B17 protein or nucleic acid, in a subject sample is optionally compared to detection of the protein or nucleic acid in a control sample. Control samples may be obtained from one or more control subjects, for example.

The term "control subject" refers to an individual having no deletion mutation of UGT2B17, also referred to as "wild-type."

In some embodiments, a biological sample is obtained from a subject to aid in determining therapeutic efficacy of exemestane treatment in the subject. The subject may currently be under treatment with exemestane or treatment with exemestane may be contemplated. For example, a subject may have a condition or disorder for which exemestane treatment is indicated such that the subject is in need thereof.

An individual subject treated and/or to be treated with exemestane has or is at risk of having a condition or disease for which inhibition of aromatase activity is desirable, such as estrogen-responsive breast cancer, endometrial cancer, endometriosis and/or ovarian cancer.

In other cases, the subject is not under treatment with exemestane and has no known condition or disorder for which exemestane treatment is indicated such that the subject is not in need thereof. Methods according to embodiments of the present invention are used in conjunction with a sample from a subject not in need of exemestane at the time the sample is obtained to aid in determining therapeutic efficacy of exemestane treatment in the subject in the case such treatment is required in the future. Thus, for example, methods according to the present invention are performed on a sample obtained from the subject at any time, such as prenatally, during infancy, childhood, or any other time to aid in determining therapeutic efficacy of exemestane treatment in the subject if such treatment is contemplated during the lifetime of the subject.

Methods according to embodiments of the present invention to aid in determining therapeutic efficacy of exemestane treatment can be performed alone or as part of a panel of biomarkers, such as, but not limited to, biomarkers of disease and/or biomarkers of therapeutic efficacy of various drugs.

Methods of detecting of UGT2B17 expression and/or function include detection of a UGT2B17 gene deletion polymorphism in the subject according to embodiments of the present invention.

Methods for detection of a deletion mutation in a gene of an individual are well-known in the art. The term in "deletion mutation" encompasses gene deletion polymorphisms and refers to a segment of the genome that is present in some individuals of a species and absent in others. Deletion mutations can be present in one or more exons, introns or regulatory regions that control expression of a gene. A deletion mutation can vary in size and can be 50 bp, 100 bp, 200 bp, 300 bp, 400 bp, 500 bp, 600 bp, 700 bp, 800 bp, 900 bp, 1000 bp, 2 kb, 3 kb, 4 kb, 5 kb, 7 kb, 8 kb, 9 kb, 10 kb, 100 kb, 110 kb, 120 kb, 130 kb, 140 kb, 150 kb, 200 kb, 300 kb, 400 kb, 500 kb, 600 kb, 700 kb, 800 kb, 900 kb, 1000 kb or more in length.

In preferred embodiments, methods according to embodiments of the present invention include detection of a UGT2B17 gene deletion polymorphism in the subject which reduces UGT2B17 expression and/or UGT2B17 activity to glucuronidate at least one metabolite of exemestane, particularly 17-dihydroexemestane.

The term "UGT2B17 expression" is used herein to refer to production of UGT2B17 nucleic acids or protein by a cell in the subject. The term "UGT2B17 nucleic acids" encompasses genomic DNA sequences encoding UGT2B17 protein, precursor UGT2B17 protein or UGT2B17 mRNA as well as regulatory nucleic acid sequences that control UGT2B17 expression. Regulatory nucleic acid sequences that control UGT2B17 expression encompass, for example, promoter elements. Regulatory nucleic acid sequences are generally located in the non-coding regions of a gene, such as in 5' non-coding regions, 3' non-coding regions and, in some cases, in introns. The term "UGT2B17 nucleic acids" encompasses mRNA encoding UGT2B17 protein and precursor UGT2B17 protein.

A common UGT2B17 deletion mutation of about 120 kb is well known in the art as described in Gallagher et al, Cancer Detect. Prev., 31:310-315, 2007; Murata et al, J. Exp. Med., 197:1279-1289, 2003; Lazarus et al, Pharmacogenet. Genomics, 15:769-778, 2005; Park et al, Cancer Epidemiol. Biomarkers Prev., 15:1473-1478, 2006; McCarroll et al, Nature Genet., 38:86-92, 2006; and Wilson et al, Genomics, 84:717-714, 2004. The homozygous UGT2B17 deletion mutation (*2/*2) has a prevalence of about 12% according to population estimates.

A homozygous deletion mutation refers to deletion mutation of the UGT2B17 locus on both chromosomes in a genome of a subject, while a heterozygous deletion mutation (*1/*2) is a deletion mutation of the UGT2B17 locus present on only one chromosome of the chromosomal pair. The term "wild-type" refers to a subject lacking a deletion mutation of the UGT2B17 locus (*1/*1).

Characterization of a nucleic acid to detect a UGT2B17 deletion mutation and/or to detect altered expression of a UGT2B17 nucleic acid in a biological sample of an individual subject is accomplished using any of various well-known techniques, such as polymerase chain reaction (PCR), fluorescent in-situ hybridization (FISH), Southern blot analysis, Northern blot analysis, RNase protection assay, pulsed-field gel electrophoresis (PFGE), direct DNA sequencing and microarray analysis.

Nucleic acids, such as mRNA, cDNA or genomic DNA characterized to detect a UGT2B17 deletion mutation and/or to detect altered expression in a method described herein are obtained by any of various techniques well-known in the art, exemplified by techniques described in J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; and Maliga, P., Methods in Plant Molecular Biology, Cold Spring Harbor Laboratory Press, New York, 1995.

Polymerase chain reaction (PCR) is a well-known method of detecting a deletion mutation in a nucleic acid. As used herein, the term PCR refers to well-known molecular biology techniques, disclosed, for example, in U.S. Pat. Nos. 4,683,195 4,683,202, and 4,965,188.

For example, oligonucleotide primers are designed to flank the UGT2B17 gene, a portion thereof, or a known deletion mutation in the UGT2B17 gene for amplification of the nucleic acid and detection of a deletion mutation therein. In a further example, oligonucleotide primers are designed such that at least one of the primers hybridizes within the nucleic acid region deleted in individuals having the deletion mutation such that no amplification occurs in samples of nucleic acids having the deletion mutation.

For example, a first set of primers is used to produce a first amplification product including a portion of the UGT2B17 present in a biological sample which does not have a deletion mutation and a second set of primers is used which produces a second product only when the deletion mutation is present in the biological sample. A first probe having a detectable label is used to detect and/or quantitate the first product and a second probe having a detectable label is used to detect and/or quantitate the second product.

In a particular example illustrated in FIG. 1, a first set of primers, TGAAAATGTTCGATAGATGGACATATAGTA, SEQ ID No. 1; and GACATCAAATTTTGACTCTTG-TAGTTTTC, SEQ ID No. 2, is used to produce a first PCR amplification product including exon 1 of UGT2B17 present in a biological sample which does not have a deletion mutation. A second set of primers, TTTAATGTTTTCTGCCT-TATGCCAC, SEQ ID No. 4; and AGCCTATG-CAATTTTCATTCAACATAG, SEQ ID No. 5, is used which flank the common 120 kb deletion mutation of UGT2B17 and produces a second PCR amplification product only when the deletion mutation is present in the biological sample. A first probe having a detectable label, TACATTTTGGT-CATATTTTTCACAACTACAAGAATTGT, SEQ ID No. 3, is used to detect and/or quantitate the first product and a second probe having a detectable label, ACTACACT-GAGATTTACAAAAGAATTCTGTCAGGATATAG, SEQ ID No. 6, is used to detect and/or quantitate the second product.

Amplification products of PCR can be analyzed, such as by gel electrophoresis, fluorescent detection, and/or sequencing to detect the presence or absence of a deletion mutation. Analysis of PCR products can also be used to detect whether a subject having a deletion mutation is homozygous or heterozygous for the deletion mutation.

PCR primers and methods for their design are well-known in the art, for example, as described in Yuryev, A., PCR Primer Design, Methods in Molecular Biology, Humana Press, 2007.

Examples of PCR methods and primers used to detect a common UGT2B17 deletion of about 120 kb are described in Lazarus et al, Pharmacogenet. Genomics, 15:769-778, 2005; Gallagher et al, Cancer Detect. Prev., 31:310-315, 2007; and in Examples detailed herein.

FISH is a well-known technique used to detection presence or absence of deletion mutations which can be used to detect UGT2B17 deletion mutations. FISH allows for visualization of a fluorescent probe to a chromosome in situ in order to detect the presence or absence of a binding site for the probe. Typically, the probe is a fluorescently labeled nucleic acid probe which specifically hybridizes to a target nucleic acid to indicate presence or absence of the target nucleic acid.

Southern blot analysis is a well-known method for detection of a target nucleic acid and is useful in detection of UGT2B17 deletion mutations. Southern blot analysis includes electrophoretic separation of nucleic acids in a sample, transfer to a membrane and hybridization with a detectably labeled probe specific for the target nucleic acid sequence. Southern blot analysis can be used in conjunction with restriction fragment length polymorphism (RFLP) if desired.

RFLP is a well-known method for detection of a target nucleic acid and is useful in detection of UGT2B17 deletion mutations. RFLP methods involve digestion of sample nucleic acids with a restriction endonuclease to produce fragments of the nucleic acids. Analysis of the sizes of the fragments allows for detection of deletion mutations due to presence or absence of restriction endonuclease sites in the nucleic acids that differ specifically between nucleic acids of subjects having the deletion mutation and subject without the deletion mutation. As is appreciated by those of skill in the art, the choice of restriction endonuclease used depends on the nucleic acids to be analyzed.

Sequencing can be used to detect UGT2B17 deletion mutations. Sequencing refers to methods of determining the ordered linear sequence of nucleotides or amino acids in a nucleic acid or protein, respectively. Nucleic acid sequencing includes manual and automated techniques using any of various well-known methods including, but not limited to, Maxam-Gilbert sequencing, also known as chemical sequencing; chain tee ruination methods of sequencing, also known as Sanger sequencing; and dye terminator sequencing. Methods of determining the amino acid sequence of a protein or peptide include chemical methods such as Edman degradation.

These and other well-known techniques for detecting deletion mutations are described in detail in standard texts such as E. Harlow and D. Lane, Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; B. K. C. Lo, Antibody Engineering: Methods and Protocols, Methods in Molecular Biology, Humana Press, 2003; F. M. Ausubel et al., Eds., Short Protocols in Molecular Biology, Current Protocols, Wiley, 2002; Crowther, J. R., The ELISA Guidebook (Methods in Molecular Biology), Humana Press, 2000; Wild, D., The Immunoassay Handbook, 3rd Edition, Elsevier Science, 2005; J. Sambrook and D. W. Russell, Molecular Cloning: A Laboratory Manual, Cold Spring Harbor Laboratory Press, 3rd Ed., 2001; and Innis et al., PCR Protocols: A Guide to Methods and Applications, Academic Press, 1990.

Methods according to embodiments of the present invention include detection of a UGT2B17 amino acid sequence having at least 95% amino acid sequence identity, at least 96% amino acid sequence identity, at least 97% amino acid sequence identity, at least 98% amino acid sequence identity, at least 99% amino acid sequence identity, or greater amino acid sequence identity with SEQ ID No.7.

Methods according to embodiments of the present invention include detection of a UGT2B17 nucleic acid sequence which specifically hybridizes under highly stringent conditions with SEQ ID No.8 or a portion thereof.

The terms "hybridizing" and "hybridization" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. High stringency hybridization conditions are those which only allow hybridization of highly complementary nucleic acids. Determination of stringent hybridization conditions is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. The terms "specific hybridization," "specifically hybridizes" and grammatical equivalents refer to hybridization of a particular nucleic acid to a target nucleic acid without substantial hybridization to nucleic acids other than the target nucleic acid in a sample.

An example of highly stringent hybridization conditions are: hybridization in a solution containing 6×SSC, 5× Denhardt's solution, 30% formamide, and 100 micrograms/ml denatured salmon sperm DNA at 37° C. overnight followed by washing in a solution of 0.1×SSC and 0.1% SDS at 60° C. for 15 minutes.

Methods according to embodiments of the present invention include detection of a UGT2B17 nucleic acid sequence encoding the amino acid sequence of SEQ ID No. 7 or a UGT2B17 amino acid sequence having at least 95% amino acid sequence identity, at least 96% amino acid sequence identity, at least 97% amino acid sequence identity, at least 98% amino acid sequence identity, at least 99% amino acid sequence identity, or greater amino acid sequence identity with SEQ ID No.7. One of skill in the art will recognize that, due to the degeneracy of the genetic code, multiple nucleic acid sequences can encode the protein of SEQ ID No. 7 and detection of such alternate sequence is encompassed by methods of the present invention.

Percent identity is determined by comparison of amino acid or nucleic acid sequences, including a reference UGT2B17 amino acid or nucleic acid sequence and a putative homologue amino acid or nucleic acid sequence. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). The two sequences compared are generally the same length or nearly the same length.

The determination of percent identity between two sequences can also be accomplished using a mathematical algorithm. Algorithms used for determination of percent identity illustratively include the algorithms of S. Karlin and S. Altshul, PNAS, 90:5873-5877, 1993; T. Smith and M. Waterman, Adv. Appl. Math. 2:482-489, 1981, S. Needleman and C. Wunsch, J. Mol. Biol., 48:443-453, 1970, W. Pearson and D. Lipman, PNAS, 85:2444-2448, 1988 and others incorporated into computerized implementations such as, but not limited to, GAP, BESTFIT, FASTA, TFASTA; and BLAST, for example incorporated in the Wisconsin Genetics Software Package, Genetics Computer Group, 575 Science Drive, Madison, Wis.) and publicly available from the National Center for Biotechnology Information.

A non-limiting example of a mathematical algorithm utilized for the comparison of two sequences is the algorithm of Karlin and Altschul, 1990, PNAS 87:2264 2268, modified as in Karlin and Altschul, 1993, PNAS. 90:5873 5877. Such an algorithm is incorporated into the NBLAST and XBLAST programs of Altschul et al., 1990, J. Mol. Biol. 215:403. BLAST nucleotide searches are performed with the NBLAST nucleotide program parameters set, e.g., for score=100, wordlength=12 to obtain nucleotide sequences homologous to a nucleic acid molecules of the present invention. BLAST protein searches are performed with the) (BLAST program parameters set, e.g., to score 50, wordlength=3 to obtain amino acid sequences homologous to a protein molecule of the present invention. To obtain gapped alignments for comparison purposes, Gapped BLAST are utilized as described in Altschul et al., 1997, Nucleic Acids Res. 25:3389 3402. Alternatively, PSI BLAST is used to perform an iterated search which detects distant relationships between molecules (Id.). When utilizing BLAST, Gapped BLAST, and PSI Blast programs, the default parameters of the respective programs (e.g., of XBLAST and NBLAST) are used (see, e.g., the NCBI website). Another preferred, non-limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used.

The percent identity between two sequences is determined using techniques similar to those described above, with or without allowing gaps. In calculating percent identity, typically only exact matches are counted.

Any method for detecting expression and/or function of UGT2B17 can be used according to embodiments of the present invention, including for example, methods for detection of UGT2B17 protein and methods for detection of UGT2B17 activity.

For example, immunoassay can be used to detect UGT2B17 protein. Particular methods of immunoassay are known in the art and illustratively include enzyme-linked immunosorbent assay (ELISA), immunoblot, immunoprecipitation, immunocytochemistry, and radioimmunoassay. Assay methods may be used to obtain qualitative and/or quantitative results. Specific details of suitable assay methods for both qualitative and quantitative assay of a sample are described in standard references, illustratively including E. Harlow and D. Lane, Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; B. K. C. Lo, Antibody Engineering: Methods and Protocols, Methods in Molecular Biology, Humana Press, 2003; F. M. Ausubel et al., Eds., Short Protocols in Molecular Biology, Current Protocols, Wiley, 2002; S. Klussman, Ed., The Aptamer Handbook: Functional Oligonucleotides and Their Applications, Wiley, 2006; Ormerod, M. G., Flow Cytometry: a practical approach, Oxford University Press, 2000; Givan, A. L., Flow Cytometry: first principles, Wiley, New York, 2001; Gorczyca, W., Flow Cytometry in Neoplastic Hematology: morphologic-immunophenotypic correlation, Taylor & Francis, 2006; and J. Sambrook and D. W. Russell, Molecular Cloning: A Laboratory Manual, Cold Spring Harbor Laboratory Press, 3rd Ed., 2001.

Antibodies directed against UGT2B17 can be polyclonal or monoclonal antibodies. Suitable antibodies also include chimeric antibodies, humanized antibodies, and antigen binding antibody fragments and molecules having antigen binding functionality, such as aptamers. Examples of antibody fragments that can be use in embodiments of inventive assays include Fab fragments, Fab' fragments, F(ab')$_2$ fragments, Fd fragments, Fv fragments, scFv fragments, and domain antibodies (dAb).

Antibodies and methods for preparation of antibodies are well-known in the art. Details of methods of antibody generation and screening of generated antibodies for substantially specific binding to an antigen are described in standard references such as E. Harlow and D. Lane, Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; and B. K. C. Lo, Antibody Engineering: Methods and Protocols, Methods in Molecular Biology, Humana Press, 2003.

Aptamers can be used to assay UGT2B17. The term "aptamer" refers to a peptide and/or nucleic acid that substantially specifically binds to a specified substance. In the case of a nucleic acid aptamer, the aptamer is characterized by binding interaction with a target other than Watson/Crick base pairing or triple helix binding with a second and/or third nucleic acid. Such binding interaction may include Van der Waals interaction, hydrophobic interaction, hydrogen bonding and/or electrostatic interactions, for example. Similarly, peptide-based aptamers are characterized by specific binding to a target wherein the aptamer is not a naturally occurring ligand for the target. Techniques for identification and generation of peptide and nucleic acid aptamers and their use are known in the art as described, for example, in F. M. Ausubel et al., Eds., Short Protocols in Molecular Biology, Current Protocols, Wiley, 2002; S. Klussman, Ed., The Aptamer Handbook: Functional Oligonucleotides and Their Applications, Wiley, 2006; and J. Sambrook and D. W. Russell, Molecular Cloning: A Laboratory Manual, Cold Spring Harbor Laboratory Press, 3rd Ed., 2001.

Optionally, spectrometric analysis is used to assay a sample for UGT2B17. For example mass analysis can be used in an assay according to embodiments of the present invention. Mass analysis is conducted using, for example, time-of-flight (TOF) mass spectrometry or Fourier transform ion cyclotron resonance mass spectrometry. Mass spectrometry techniques are known in the art and exemplary detailed descriptions of methods for protein and/or peptide assay are found in Li J., et al., Clin Chem., 48(8):1296-304, 2002; Hortin, G. L., Clinical Chemistry 52: 1223-1237, 2006; Hortin, G. L., Clinical Chemistry 52: 1223-1237, 2006; A. L. Burlingame, et al. (Eds.), Mass Spectrometry in Biology and Medicine, Humana Press, 2000; and D. M. Desiderio, Mass Spectrometry of Peptides, CRC Press, 1990.

Exemplary methods for assessment of UGT activity, including UGT2B17 activity, include UGT enzyme functional assays such as described herein, for example as described in Example 8. In particular embodiments, assay of UGT2B17 activity includes assay of activity to glucuronidate 17-dihyroexemestane.

The term "detectable label" refers to a substance that can be measured and/or observed, visually or by any appropriate method illustratively including spectroscopic, optical, photochemical, biochemical, enzymatic, electrical and/or immunochemical methods of detection, to indicate presence of the label. Non-limiting examples of detectable labels that can be used in conjunction with methods described herein illustratively include a fluorescent moiety, a chemiluminescent moiety, a bioluminescent moiety, a magnetic particle, an enzyme, a substrate, a radioisotope and a chromophore. For example, probes and/or primers can be labeled with a dye, such as a fluorophore, a chromophore, a radioactive moiety or a member of a specific binding pair such as biotin. The term "member of a specific binding pair" refers to a substance that specifically recognizes and interacts with a second substance exemplified by specific binding pairs such as biotin-avidin, biotin-streptavidin, antibody-antigen, and target-aptamer. Non-limiting examples of detectable labels that can be used include fluorescent dyes such as fluorescein and its derivatives, rhodamine and its derivatives, Texas Red, BODIPY dyes including but not limited to BODIPY-FL, BODIPY-TR, BODIPY-TMR, BODIPY-630/650, BODIPY-650/670; 5'carboxy-fluorescein ("FMA"), 6-carboxy-4',5'-dichloro-2',7'-dimethoxyfluorescein, succinimidyl ester ("JOE"), 6-carboxytetramethylrhodamine ("TAMRA"), 6Ncarboxy-X-rhodamine ("ROX"), HEX, TET, IRD40, IRD41, cyanine dyes such as Cyanine 3 and Cyanine 5, and ALEXA dyes, including but not limited to ALEXA-488, ALEXA-532, ALEXA-546, ALEXA-568, and ALEXA-594; chromophores such as horseradish peroxidase, alkaline phosphatase and digoxigenin; and radioactive moieties such as $^{32}P$, $^{35}S$, $^{3}H$, $^{125}I$ or $^{14}C$; and binding partners such as biotin and biotin derivatives.

Methods are provided according to embodiments of the present invention for detecting exemestane use in a subject. In general, methods of detecting exemestane use in a subject include assay for a glucuronidated metabolite of exemestane in urine. For example, a urine sample is obtained from a subject and assayed for glucuronidated 17-dihydroexemestane.

Detection of the glucuronidated 17-dihydroexemestane is indicative of exemestane use by the subject. However, a negative or ambiguously weak positive detection of the glucuronidated 17-dihydroexemestane is not dispositive for non-use of exemestane by the subject since this depends on whether the subject has a functioning UGT2B17 protein. Thus, a sample obtained from the subject is assayed for a UGT2B17 gene deletion polymorphism, UGT2B17 expression and/or UGT2B17 function.

For example, real-time PCR is performed on genomic DNA in a sample obtained from the subject as described in Example 1. If the subject has been using exemestane, detection of the UGT2B17 gene deletion polymorphism is indicative that a blood sample obtained from the subject should be assayed for exemestane, since the urine test is not an accurate indicator of exemestane use in subjects having no functional UGT2B17. Thus, exemestane use, such as illicit exemestane use by an athelete is detected in subjects lacking functional UGT2B17 where the urine test for UGT2B17 metabolites fails or is ambiguous.

Embodiments of kits according to the present invention optionally include one or more components for use in an assay of the present invention such as a UGT2B17 primer, antibody or aptamer, a liquid such as a buffer and/or solution used in an assay, a container, a detectable label for labeling an antibody or aptamer directly or indirectly, a standard, a negative control and a positive control.

Embodiments of inventive compositions and methods are illustrated in the following examples. These examples are provided for illustrative purposes and are not considered limitations on the scope of inventive compositions and methods.

EXAMPLES

Example 1

Genotyping to Detect UGT2B17 Gene Deletion

A high-throughput genotyping assay using real-time PCR with allelic discrimination is used in this example. Each reaction includes two primers and one 6-FAM-labeled probe to amplify exon 1 of UGT2B17, and two primers and one JOE-NHS-Ester-labeled probe (that spans the deletion cut site) that amplify only if the deletion is present (FIG. 1).

FIG. 1 shows gene structure and primer and probe locations for the UGT2B17 multiplex real-time PCR assay. The roman numerals I-VI indicate the exons of the UGT2B17 gene on the wild-type allele. The deletion allele as shown in FIG. 1 the wild-type allele indicating the 120 kb that are deleted, including the entire UGT2B17 gene. Red arrows indicate the primers that will amplify the deletion allele and the red bar (with fluorescent label Joe) indicates the deletion probe. Blue arrows indicate the primers that will amplify exon 1 of UGT2B17 from the wild-type allele and the blue bar (with fluorescent label Fam) indicates the deletion probe.

Due to high sequence homology between UGT2B17 and other UGT genes and pseudogenes, primers are designed using Blast 2.2.14 (http://www.ncbi.nlm.nih.gov/BLAST/) maximizing for 3' sequence mismatches with other homologous genes, and primers are obtained from Integrated DNA Technologies (Coralville, Iowa). Table I shows exemplary primers that can be used.

Table I

| Primer and probe sequences for a UGT2B17 genotype assay | |
|---|---|
| primer name | primer composition (5' to 3') |
| Exon 1-forward | TGAAAATGTTCGATAGATGGACATATAGTA, SEQ ID No. 1 |
| Exon 1-reverse | GACATCAAATTTTGACTCTTGTAGTTTTC, SEQ ID No. 2 |
| Exon 1-probe | 6-FAM-TACATTTTGGTCATATTTTTCACA ACTACAAGAATTGT-BHQ1, SEQ ID No. 3 |

Table I-continued

| Primer and probe sequences for a UGT2B17 genotype assay | |
|---|---|
| primer name | primer composition (5' to 3') |
| Deletion-forward | TTTAATGTTTTCTGCCTTATGCCAC, SEQ ID No. 4 |
| Deletion-reverse | AGCCTATGCAATTTTCATTCAACATAG, SEQ ID No. 5 |
| Deletion-probe | JOE-ACTACACTGAGATTTACAAAAGAATT CTGTCAGGATATAG-BHQ1, SEQ ID No. 6 |

Reactions (20 µl) are performed in 384-well plates using the ABI 7900 HT Sequence Detection System, with incubations at 50° C. for 2 min; 95° C. for 15 min; and 40 cycles of 94° C. for 1 min, 60° C. for 1 min 30 sec. Reactions include QuantiTect Multiplex PCR Master Mix (1× final concentration; Qiagen, Valencia, Calif.), 0.4 µM for each primer, 0.2 µM for each probe, and 20-100 ng of DNA. Negative controls (no DNA template) are run on every plate and genotypes are assigned by the automatic calling feature of the allelic discrimination option in SDS 2.2.2 software (Applied Biosystems, Foster City, Calif.).

Example 2

Chemicals and Materials

Exemestane is purchased from Hangzhou HETD Industry Co. LTD (Zhejiang, China). UDPGA, alamethicin, and β-glucuronidase are purchased from Sigma-Aldrich (St. Louis, Mo.) and [$^{14}$C] UDPGA (200 mCi/mmol) is purchased from American Radiolabeled Chemicals (St. Louis, Mo., USA). The NADPH regenerating system (including solutions A [26.1 mM NADP, 66 mM glucose-6-phosphate, and 66 mM MgCl$_2$] and B [40U/ml glucose-6-phosphate dehydrogenase, 5 mM sodium citrate]) is purchased from BD Biosciences (Woburn, Mass.). Androst-[4-$^{14}$C]-ene-3,17-dione is purchased from Perkin Elmer (Boston, Mass.). The high-performance liquid chromatography (HPLC) scintillation solution, Ecoscint Flow, is purchased from National Diagnostics (Atlanta, Ga., USA) while Dulbecco's phosphate-buffered saline (minus calcium-chloride and magnesium-chloride), fetal bovine serum (FBS), penicillin-streptomycin and geneticin (G418) are all purchased from Gibco (Grand Island, N.Y.). The Platinum® Pfx DNA polymerase and the pcDNA3.1/V5-His-TOPO mammalian expression vector are obtained from Invitrogen (Carlsbad, Calif.) while the QIAEX® II gel extraction kit is purchased from Qiagen (Valencia, Calif.). The BCA protein assay kit is purchased from Pierce (Rockford, Ill.). Aromatase transfection-ready cDNA is purchased from Origene (Rockville, Md.) and the anti-aromatase antibody is purchased from Abcam (Cambridge, Mass.). The human UGT1A Western blotting kit that includes an anti-UGT1A polyclonal antibody, and UGT2B7 protein standard, are purchased from Gentest (Woburn, Mass.). The anti-β-actin monoclonal antibody is purchased from Sigma (St. Louis, Mo.). All other chemicals used in these studies are purchased from Fisher Scientific (Pittsburgh, Pa.) unless otherwise specified.

Example 3

Tissues and Cell Lines

Normal human liver tissue specimens used for these studies are described in Wiener, D. et al., *Cancer Res*, 64: 1190-6, 2004. Briefly, tissues are quick-frozen at −70° C. within 2 hours post-surgery. Liver microsomes are prepared through differential centrifugation as described in Coughtrie, M. et al., *Anal Biochem*, 159: 198-205, 1986 and are stored (10-20 mg protein/ml) at −80° C. Genomic DNA is extracted from each of the same liver specimens from nuclei isolated during the microsome purification process. Microsomal protein concentrations are measured using the BCA assay. UGT2B17 genotyping for all liver genomic DNA specimens and UGT2B17 mRNA expression in the same human liver are performed by real-time PCR as described in Example 1 and in Gallagher, C. et al., *Cancer Epidemiol Biomarkers Prev;* 16: 823-8, 2007; and Balliet, R. et al., *Cancer Res*, 69: 2981-9, 2009.

An aromatase-overexpressing HEK293 cell line (termed HEK293-aro) is generated for aromatase activity assays. Using the aromatase cDNA-containing pCMV6-XL4 vector from Origene as template (100 ng), aromatase cDNA is PCR-amplified using Pfx DNA polymerase (1.25 units; Invitrogen, Carlsbad, Calif.), 0.3 mM of each dNTPs, and 20 pmol each of sense (5'-CCAGACGTCGCGACTCTAAATTG-3') (SEQ ID NO:9) and antisense (5'-CTGTGAGGATGACACTAT-TGGC-3') (SEQ ID NO:10) primers, corresponding to nucleotides -49 to -26 and +1580 to +1601, respectively, relative to the aromatase translation start site. PCR amplification of aromatase cDNA is performed in a GeneAmp 9700 thermocycler (Applied Biosystems, Foster City, Calif.) using as follows: 1 cycle of 94° C. for 2 min, 35 cycles of 94° C. for 15 s, 58° C. for 30 s, and 68° C. for 2 min, followed by a final cycle of 68° C. for 10 min. After a subsequent post-amplification step using Taq DNA polymerase (10 min at 72° C.; Denville Scientific, South Plainfield, N.J.) to ensure the addition of 3'-overhanging adenines, the PCR product (1793 bp) is purified after electrophoresis in 1.5% agarose using the QIAEX® II gel extraction kit (Qiagen, Valencia, Calif.) and sequenced in full using the same aromatase PCR primers. The PCR product is subsequently sub-cloned into the pcDNA3.1/V5-His-TOPO mammalian expression vector using standard methodologies. The cloned vector is sequenced in full (using the same PCR primers described above) and transfected into HEK293 cells (purchased from ATCC; Rockville, Md.) by electroporation (200 V and 1000 µF) using 10 µg of pcDNA3.1/V5-His-TOPO/aromatase plasmid DNA with 5 ×10$^6$ HEK293 cells in 0.5 ml serum-free media in a GenePulser Xcell (Bio-Rad, Hercules, Calif.). Cells stably overexpressing the individual aromatase are selected with G418 (Invitrogen, Carlsbad, Calif.). Aromatase expression in HEK293 cells is monitored by western blot analysis, by loading 40 µg of total protein lysate of HEK293 (negative control) and HEK293-aro cells, and using the anti-aromatase antibody (#ab18995; Abcam; used in a 1:200 dilution). β-actin is used as a loading control and is monitored using a 1:5000 dilution of the monoclonal anti-β-actin antibody (Sigma-Aldrich).

Cells over-expressing individual UGT or aromatase are harvested to prepare homogenates as described in Sun, D. et al., *Drug Metab Dispos;* 35: 2006-14, 2007. Total homogenate protein concentrations are measured using the BCA protein assay.

Using western blot analysis, a non-specific band of ~42 KDa is observed in both HEK293-aro and parental HEK293 cell lysates, a clear band at 58 KDa is recognized in HEK293-aro cell homogenates which matches the expected molecular weight of aromatase; no 58 KDa band is observed in lysate of untransfected HEK293 cells.

Example 4

Western Blot Analysis of UGT Proteins

Levels of UGT1A and 2B proteins are determined by Western blot analysis as described in Sun, D. et al., *Drug Metab Dispos;* 35: 2006-14, 2007 and Wiener, D. et al., *Drug Metab Dispos*, 32: 72-9, 2004; using a 1:5000 dilution of antibody. UGT1A4 protein is detected using the UGT1A antibody from Gentest while UGT2B17 expression is measured using a newly-synthesized affinity-purified chicken anti-UGT2B antibody generated against the peptide CKWDQFYSEV-LGRPTTL (SEQ ID NO:11), which is common to all human UGT2B family members (Pocono Rabbit Farm, Canadensis, Pa.). Proteins are detected by chemiluminescence using the SuperSignal West Dura Extended Duration Substrate (Pierce Biotechnology, Inc., Rockford, Ill.). Secondary antibodies supplied with the Dura ECL kit (anti-rabbit and anti-mouse) are used at 1:3000. UGTs 1A4 and 2B17 are quantified against 100-250 ng of human UGT1A and UGT2B7 protein (Gentest), respectively, by densitometric analysis of X-ray film exposures (1 sec - 2 min) of Western blots using a GS-800 densitometer with Quantity One software (Bio-Rad, Hercules, Calif.). All cell homogenate protein levels are normalized to the levels of calnexin observed in each lane (quantified by densitometric analysis of Western blots as described above). Determinations of exemestane-17-O-glucuronide formation in UGT1A4- and UGT2B17-over-expressing cell lines are calculated relative to the levels of UGT expression in the respective cell lines. X-ray film bands are always below densitometer saturation levels as indicated by the densitometer software. Densitometric results are always consistent irrespective of the exposure time. Western blot and subsequent densitometric analysis is performed in triplicate on three separate occasions, using the same UGT-containing cell homogenates used for activity assays, with relative UGT protein levels expressed as the mean of these experiments.

Example 5

Synthesis of 17-Dihydroexemestane 17-dihydroexemestane is prepared from exemestane as described in Mareck, U. et al., *Rapid Commun Mass Spectrom*, 20: 1954-62, 2006 with minor modifications. Briefly, exemestane and NaBH$_4$ are individually dissolved in methanol/water (4:1, v/v). For reduction of the 17-keto functional group of exemestane, NaBH$_4$ is slowly added to the suspended exemestane in a 1:2 molar ratio. The mixture is left at ambient temperature for at least 1 h and then assayed by thin layer chromatography to ensure reaction completeness prior to solvent removal by vacuum. After dissolving the dry residue in 1.5M HCl, 1M KOH (500 µL) is added. The mixture is extracted by ethyl ether, dried by vacuum, and re-dissolved in 30 ml ethyl ether:hexane (1:1) at 50° C. After 3 days, the formed crystals are washed with hexane and dried by vacuum. The synthesized 17-dihydroexemestane structure is characterized by a Bruker 500 MHz nuclear magnetic resonance (NMR) spectrometer and HPLC/MS/MS, with the MS spectrum resulting in a clear peak at m/z 299 [M]$^+$ and a daughter product at m/z 135.

Both exemestane and 17-dihydroexemestane are dissolved in 100% ethanol and the stock solutions are kept at −20° C.

Figure 3A:
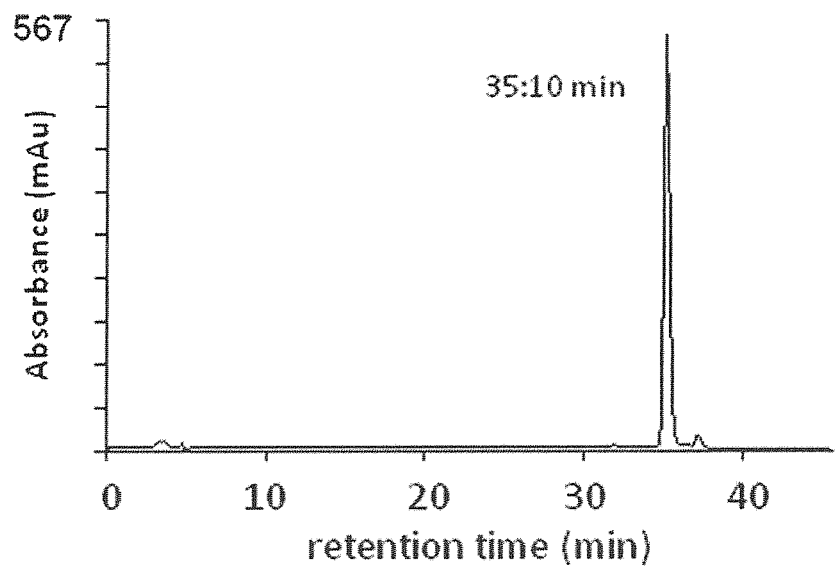
FIG. 3A is a chromatogram of 17-dihydroexemestane.
Figure 3B:
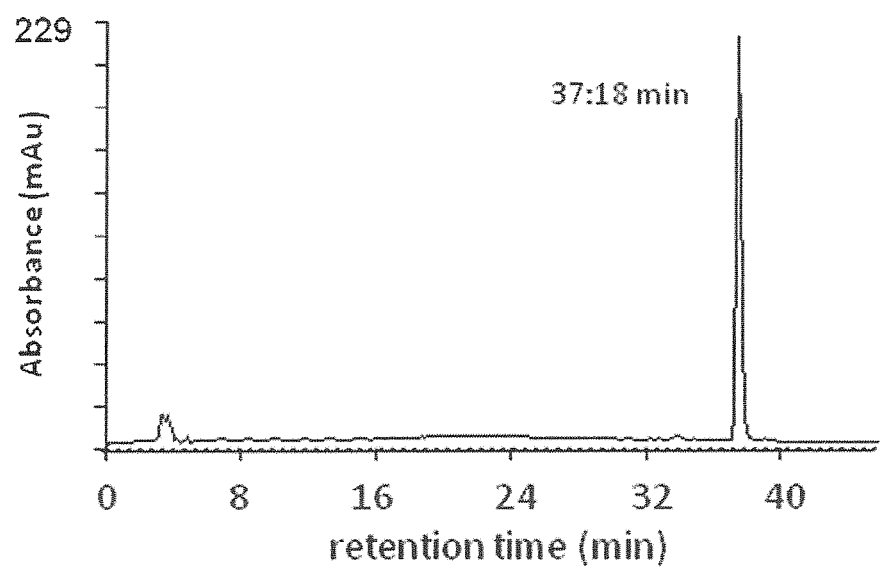
FIG. 3B is a chromatogram of exemestane
Figure 3C:
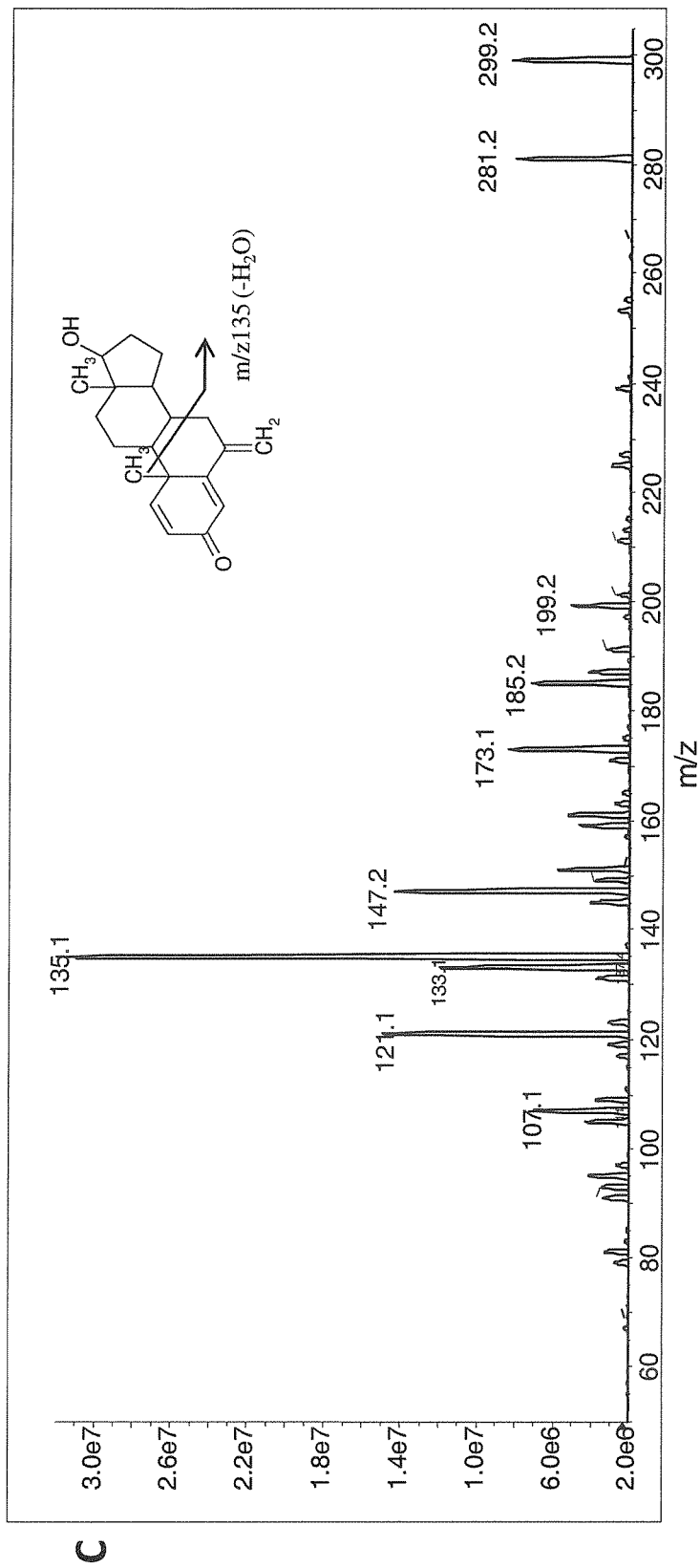
FIG. 3C is a mass spectrum of 17-dihydroexemestane.

As shown in FIG. 3A, the HPLC chromatogram revealed a 99% pure product whose retention time (35.1 min) is about 2 min shorter than the parent compound, exemestane (FIG. 3B). The product shown in FIG. 3A is characterized by UPLC/MS/MS (FIG. 3C), with the MS spectrum showing a clear [M+H]$^+$ peak at m/z 299.2, which is identical to the predicted molecular weight of 17-dihydroexemestane, and a second major fragment at m/z 135.1. The structure is further confirmed to be 17-dihydroexemestane by $^1$H NMR: $^1$H NMR (CDCl$_3$, 500 MHz) δ 0.83 (s, 3H), 1.04-1.08 (m, 1H), 1.16 (s, 3H), 1.24-1.31 (m, 1H), 1.36-1.40 (m, 1H), 1.48-1.52 (m, 1H), 1.64-1.72 (m, 4H), 1.78-1.83 (m, 3H), 1.90-1.93 (m, 1H), 2.08-2.12 (m, 1H), 2.51 (d, 1H, J=9.5 Hz), 3.68 (t, 1H, J=8.0 Hz), 4.96 (s, 1H), 5.03 (s, 1H), 6.17 (s, 1H), 6.26 (d, 1H, J=10.0 Hz), 7.11 (d, 1H, J=10.0 Hz).

Example 6

Aromatase-Inhibiting Activity Assays

Aromatase activity is determined by measuring the levels of estrone formation using androst-[4-$^{14}$C]-ene-3,17-dione (5 µM) as substrate and by HEK293-aro cell homogenates as the source of aromatase. 3.3 nM to 10 µM of exemestane and 17-dihydroexemestane are used for the determination of their aromatase inhibiting activities. Incubations are performed in 10 mM potassium phosphate (pH 7.4) buffer containing 100 mM KCl, 1 mM EDTA, 1 mM DTT, a NADPH generating system (with final concentrations of 0.26 mM NADP$^+$, 0.66 mM G6P, 0.66 mM MgCl$_2$ and 0.4 u/ml G6P dehydrogenase), 125 µg HEK293-aro cell homogenate, 5 µM androst-[4-$^{14}$C]-ene-3,17-dione and various concentrations of exemestane or 17-dihydroexemestane, in a final reaction volume of 50 µL at 37° C. for 2 h. Reactions are terminated by the addition of 50 µL cold acetonitrile on ice. Mixtures are centrifuged for 10 min at 4° C. at 16,100 g and the supernatants are collected.

Estrone formation is analyzed by radioflow-HPLC using a Gold 126 Solvent Module HPLC system (Beckman Coulter, Fullerton, Calif.) equipped with an automatic sampler (Model 508), a UV detector (Model 166) and a radioactive flow detector with 1000-µl flow cell (INUS System, Tampa, Fla.). HPLC is performed using a 5µ Luna C18 analytical column (4.6 mm×250 mm, Phenomenex, Torrance, Calif.) combined with a 5µ Gemini C18 analytical column (4.6 mm×250 mm, Phenomenex) in series with a Luna C18 guard column (4 mm L×3.0 mm ID, Phenomenex). The gradient elution conditions consisted of a flow rate of 0.5 ml/min as follows: starting with 55% acetonitrile and 45% buffer A (5 mM ammonium acetate, pH 5.0) for 5 min, a subsequent linear gradient to 75% acetonitrile/25% buffer A over 15 min is performed and then maintained at 75% acetonitrile for 10 min. The formed [$^{14}$C] estrone peak is determined by HPLC-radioactive flow detection and is confirmed by retention time comparisons with an estrone standard (Sigma-Aldrich) detected by UV. Total aromatase activity of HEK293-aro cell homogenates is determined as the ratio of the levels of estrone vs. androst-[4-$^{14}$C]-ene-3,17-dione. The concentration of each compound required to reduce the total aromatase activity by 50% (IC$_{50}$) is calculated using GraphPad Prism 5 software (Graph-Pad Software, San Diego, Calif.). HEK293 cell homogenate without overexpressed aromatase is used as a negative control. All experiments are performed in triplicate in independent assays.

Example 7

Determination of Aromatase-Inhibiting Activity of 17-Dihydroexemestane

Figure 4A:
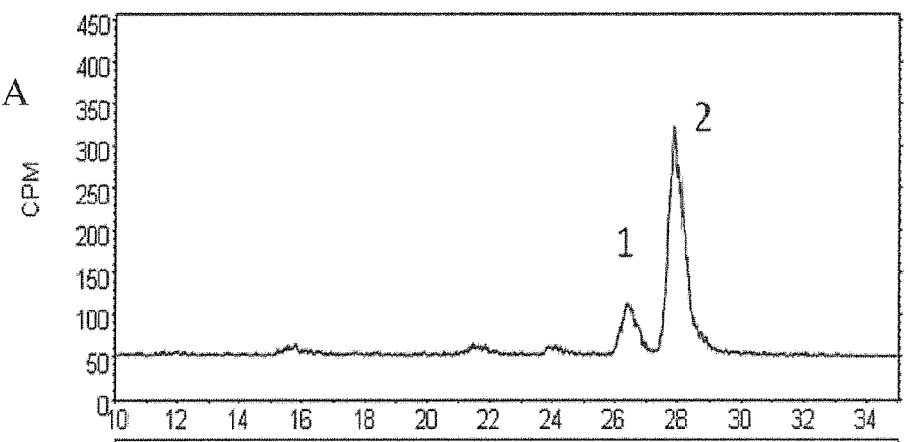
FIG. 4A is a graph showing radioflow HPLC analysis of estrone formation in HEK293-aro cells in the presence of androst-[4-$^{14}$C]-ene-3,17-dione.
Figure 4B:
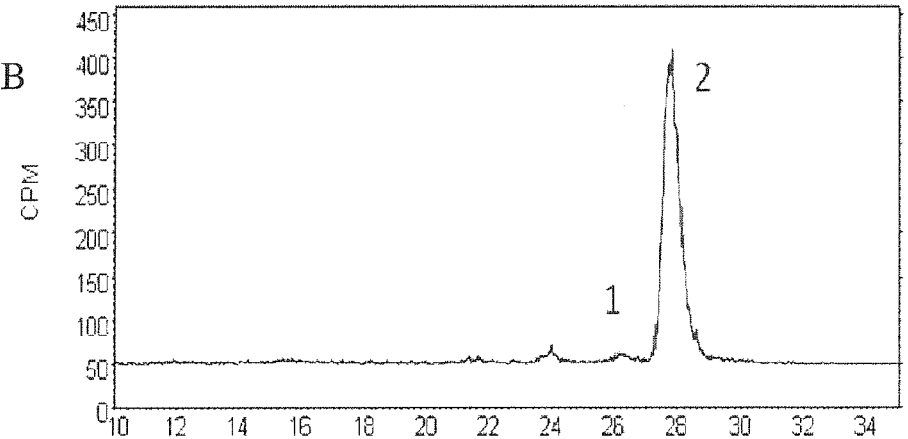
FIG. 4B is a graph showing radioflow HPLC analysis of inhibition of estrone formation in HEK293-aro cells in the presence of androst-[4-$^{14}$C]-ene-3,17-dione and 17-dihydroexemestane.
Figure 4C:
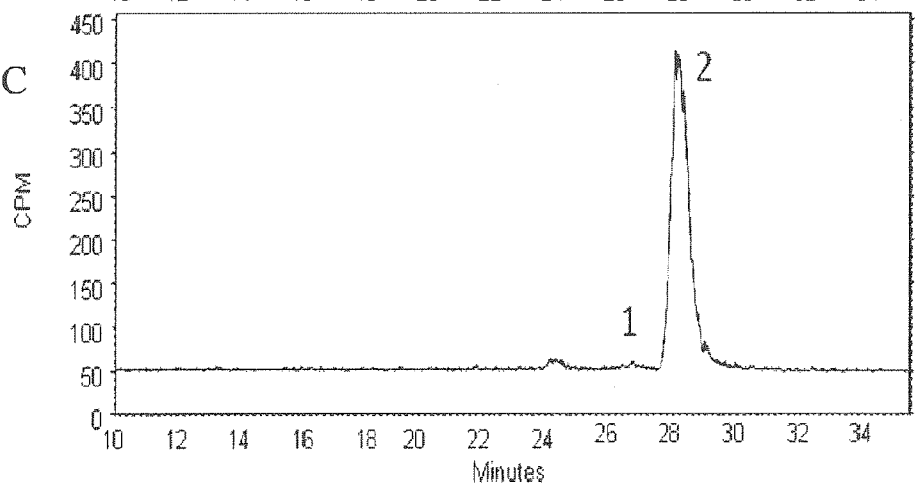
FIG. 4C is a graph showing radioflow HPLC analysis of inhibition of estrone formation in HEK293-aro cells in the presence of androst-[4-$^{14}$C]-ene-3,17-dione and exemestane.

The enzymatic activity of HEK293-aro cells is determined using HPLC by measuring the formation of estrone from androst-4-ene-3,17-dione in incubations with HEK293-aro cell homogenate±exemestane or 17-dihydroexemestane. As shown in FIGS. 4A-4C, an obvious estrone peak is observed when no exemestane or 17-dihydroexemestane added, FIG. 4A. The aromatase enzymatic activity is inhibited by both 17-dihydroexemestane, FIG. 4B and the parent compound, exemestane, FIG. 4C. The IC$_{50}$ values for exemestane (1.4±0.42) µM and 17-dihydroexemestane (2.3±0.83) µM are comparable and not statistically different (p=0.15).

Example 8

Glucuronidation Assays

For all glucuronidation assays, cell line homogenate (100 µg-1 mg protein) or human liver microsomes (HLM; 2.5 µg-10 µg protein) are pre-incubated with alamethicin (50 µg/mg protein) for 15 min in an ice bath. Glucuronidation reactions are performed in a final reaction volume of 50 µL at 37° C. for 60 mm in 50 mM Tris-HCl buffer (pH 7.4), 10 mM MgCl$_2$, 4 mM UDPGA with 1 µL (2% ethanol: v/v) 17-dihydroexemestane or exemestane. For screening of UGT-overexpressing cell lines for glucuronidating activity against exemestane and 17-dihydroexemestane, incubations containing up to 3.5 mM of exemestane or up to 600 µM 17-dihydroexemestane. For kinetic assays, 4-300 µM 17-dihydroexemestane is utilized. Reactions are terminated by the addition of 50 µL cold acetonitrile on ice. Mixtures are centrifuged for 10 min at 4° C. at 16,100 g and the supernatants are collected. Experiments are always performed in triplicate in independent assays.

17-Dihydroexemestane glucuronidation is analyzed using a Waters ACQUITY ultra-pressure liquid chromatography (UPLC) System (Milford, Mass.) with a 1.7µ ACQUITY UPLC BEH C18 analytical column (2.1 mm×50 mm, Waters, Ireland) in series with a 0.2 µm Waters assay frit filter (2.1 mm, Waters, USA). The gradient elution conditions, using a flow rate of 0.3 ml/min, are as follows: starting with 19% acetonitrile and 81% buffer A (5 mM ammonium acetate, pH 5.0) for 1 min, a subsequent linear gradient to 75% acetonitrile/25% buffer over 2 min is performed and then maintained at 75% acetonitrile for 2 min.

Exemestane-17-O-glucuronide is confirmed by its stability in 1M NaOH but sensitivity to the treatment of β-glucuronidase. In addition, incubation products (up to 5 µL) are loaded onto an UPLC/MS/MS for confirmation of exemestane-17-O-glucuronide formation. An UPLC identical to that described above is used in tandem with a Waters TQD triple quadrupole MS system. By using a positive mode, the parent compound [M+H]$^+$ peak and their glucuronide [M-Gluc.+H]$^+$ peak are characterized.

Ten HLMs are randomly-chosen from the 110 HLM panel for kinetic analysis—five from UGT2B17 (*1/*1) homozygous wild-type subjects and five from UGT2B17 (*2/*2) homozygous deletion subjects. As controls, glucuronidation assays are regularly performed using human HLMs (as a positive control for glucuronidation activity) and untransfected HK293 cell homogenate protein (as a negative control for glucuronidation activity) as described in Wiener, D. et al., *Drug Metab Dispos*, 32: 72-9, 2004; and Fang, J. et al., *Cancer Res*, 62: 1978-86, 2002.

Figure 5A:
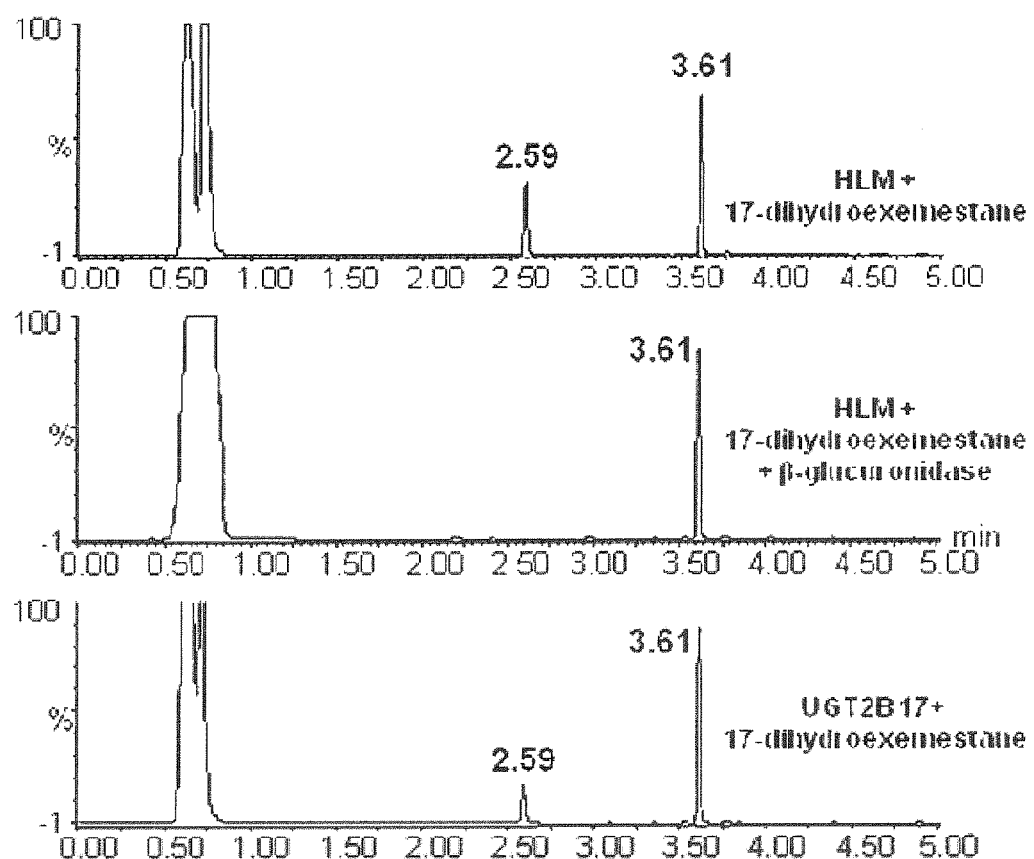
FIG. 5A is a graph showing UPLC traces using 250 μg HLM and 300 μM 17-dihydroexemestane (top trace); 250 μg HLM and 300 μM 17-dihydroexemestane incubated with β-glucuronidase (middle trace); and 250 μg UGT2B17 cell homogenates and 300 μM 17-dihydroexemestane (bottom trace)
Figure 5B:
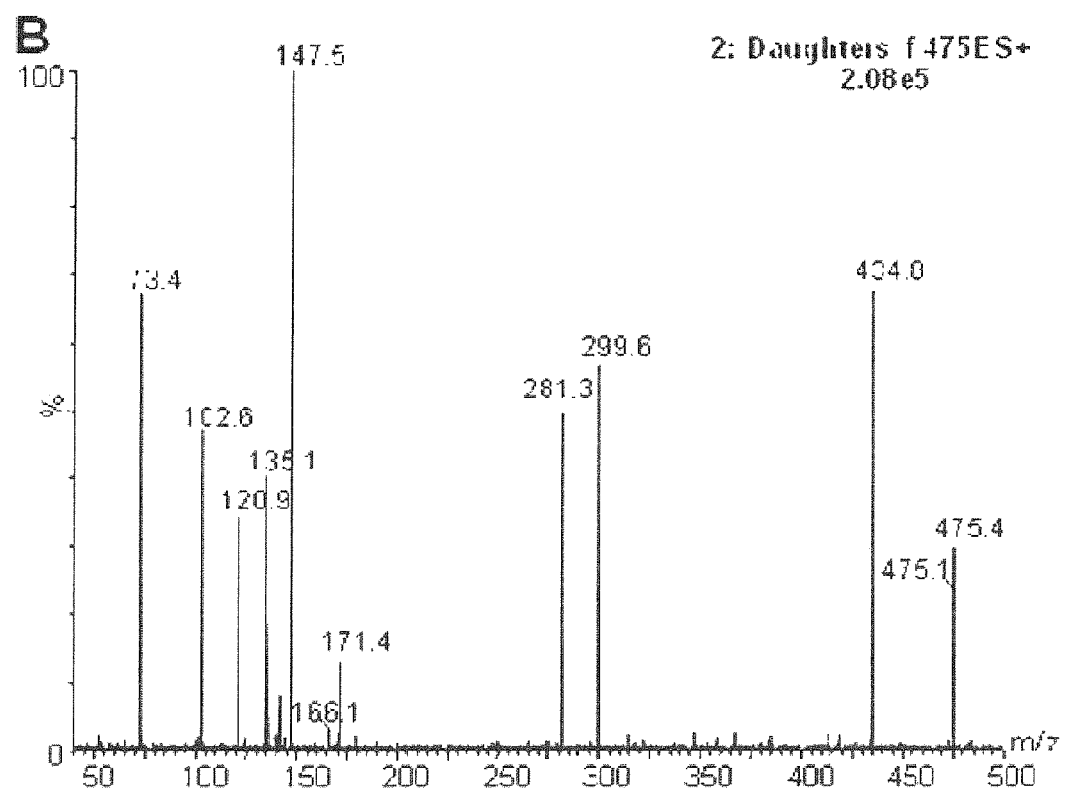
FIG. 5B shows a mass spectrum trace.
Figure 5C:
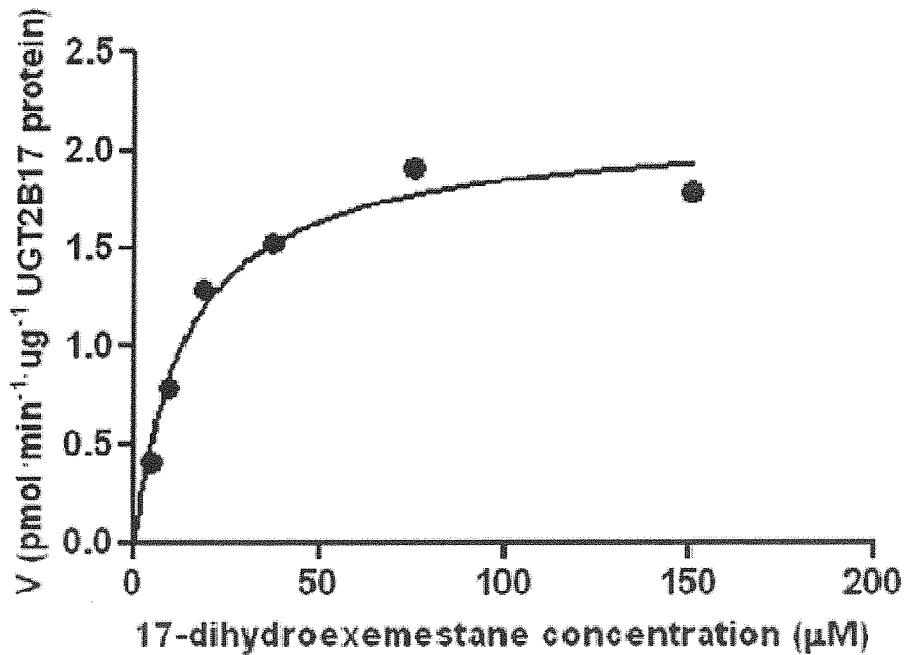
FIG. 5C is a graph showing a concentration curve for exemestane-17-O-glucuronide formation from UGT2B17-overexpressing cell homogenates.
Figure 5D:
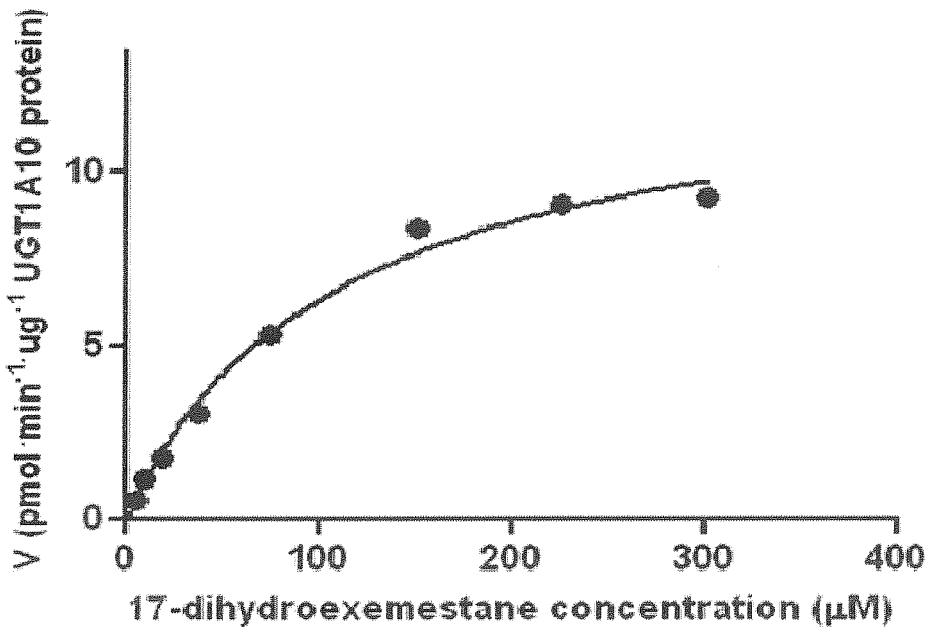
FIG. 5D is a graph showing a concentration curve for exemestane-17-O-glucuronide formation from UGT1A10-overexpressing cell homogenates.

This characterization of 17-dihydroexemestane glucuronidation by UPLC shows that in addition to a peak corresponding to the parent 17-dihydroexemestane (retention time=3.61 min), a potential glucuronide peak at a retention time of 2.59 min is observed, FIG. 5A, top trace. This peak is not sensitive to treatment with 1M NaOH but is sensitive to treatment with β-glucuronidase, suggesting that this glucuronide peak is an O-glucuronide conjugate, FIG. 5A, middle trace. The mass spectrum of this peak as determined by UPLC/MS/MS demonstrated a [M$^+$] peak at m/z 475.4 for exemestane-17-O-glucuronide (the glucuronide conjugate of 17-dihydroexemestane), a [M+H]$^+$ peak at m/z 299.6 for 17-dihydroexemestane after loss of the glucuronide acid moiety (molecular weight=176 g/mol), and a m/z 281.3 fragment after loss of a H2O molecule from 17-dihydroexemestane, FIG. 5B.

To identify the UGTs responsible for glucuronidation of 17-dihydroexemestane, homogenates from HEK293 cells individually over-expressing UGTs 1A1, 1A3, 1A4, 1A6, 1A7, 1A8, 1A9, 1A10, 2B4, 2B7, 2B10, 2B11, 2B15 and 2B17 are screened for glucuronidation activity. Four UGTs exhibited detectable activity against 17-dihydroexemestane: the hepatic UGTs 1A4 and 2B17, and UGTs 1A8 and 1A10 whose expression in liver is low or undetectable, Izukawa, T. et al., *Drug Metab Dispos,* 37: 1759-68, 2009 and Itaaho, K. et al., *Drug Metab Dispos,* 37: 768-75, 2009. None of the other UGTs screened in assays described herein exhibited any glucuronidation activity using up to 1 mg of UGT overexpressing cell homogenate. As exemplified for incubations with UGT2B17-overexpressing cell homogenates, FIG. 5A, bottom trace, the peak retention time by UPLC for all of the active UGTs is identical to that observed for exemestane-17-O-glucuronide in HLM, FIG. 5A, top trace. Representative plots of glucuronidation rate versus substrate concentration are shown in FIG. 5 for the UGTs exhibiting the highest activity against 17-dihydroexemestane, UGT2B17, FIG. 5C; UGT1A10, FIG. 5D. After normalizing for UGT expression by Western blot analysis; Sun, D. et al., *Drug Metab Dispos;* 35: 2006-14, 2007, and Dellinger, R. et al., *Carcinogenesis,* 28: 2412-8, 2007, the relative glucuronidation activity against 17-dihydroexemestane based on $V_{max}/K_M$ is UGT2B17>UGT1A10>UGT1A8>UGT1A4 shown in Table 2.

TABLE 2

Kinetic analysis of UGTs active against 17-dihydroexemestane

| UGT | $V_{max}$ (pmol · min$^{-1}$ · μg UGT protein$^{-1}$)$^a$ | $K_M$ (μM) | $V_{max}/K_M$ (nl · min$^{-1}$ · μg UGT protein$^{-1}$)$^a$ |
|---|---|---|---|
| UGT1A8 | 0.30 ± 0.06 | 14 ± 3.9 | 22 ± 2.1 |
| UGT1A10 | 12 ± 1.8 | 124 ± 15 | 100 ± 7.9 |
| UGT2B17 | 2.0 ± 0.25 | 15 ± 2.7 | 137 ± 17 |
| UGT1A4$^{24Pro/48Leu}$ | 0.27 ± 0.01 | 34 ± 3.9 | 8.1 ± 0.9 |
| UGT1A4$^{24Thr/48Leu}$ | 0.26 ± 0.04 | 28 ± 7.8 | 9.8 ± 1.9 |
| UGT1A4$^{24Pro/48Val}$ | 0.40 ± 0.03$^b$ | 36 ± 5.4 | 12 ± 2.4 |

$^a$All kinetic data for different UGT-over-expressing cell homogenates is normalized per ·μg UGT protein as determined by Western blot analysis as previously described$^{29, 30}$.
$^b$p < 0.005, as compared to UGT1A4$^{24Pro/48Leu}$.

The hepatic UGT2B17 exhibited a similar binding affinity ($K_M$=15 μM) against 17-dihydroexemestane to UGT1A8 and a significantly (p<0.001) lower $K_M$ than that observed for UGTs 1A4 and 1A10. The relative overall activity of UGT2B17 as determined by $V_{max}/K_M$ is 1.4- and 6.2-fold higher than that observed for UGTs 1A10 and 1A8, respectively, and 17-fold that observed for UGT1A4, the other active hepatic glucuronidating enzyme. While UGT1A8 exhibited a lower $K_M$ than UGT1A10, the overall activity of UGT1A10 is 4.5-fold that of UGT1A8 as determined by $V_{max}/K_M$.

Example 9

Analysis of 17-Dihydroexemestane Glucuronidation by Hepatic UGT Variants and HLM UGTs 1A4 and 2B17 are hepatic enzymes that exhibit prevalent polymorphisms that are shown to be functional in studies described in Wiener, D. et al., *Drug Metab Dispos,* 32: 72-9, 2004; and Wilson, W. et al., *Genomics,* 84: 707-14, 2004. HEK293 cell lines over-expressing the UGT1A4$^{24Pro/48Leu}$, UGT1A4$^{24Thr/48Leu}$, and UGT1A4$^{24Pro/48Val}$ variants are described in Wiener, D. et al., *Drug Metab Dispos,* 32: 72-9, 2004; Dellinger, R. et al., *Drug Metab Dispos,* 34: 943-9, 2006; and Blevins-Primeau, A. et al., *Cancer Res,* 2009. Although a significant 1.5-fold increase in $V_{max}$ is observed for the UGT1A4$^{24Pro/48Val}$ variant against 17-dihydroexemestane as compared to either of the other UGT1A4 variants, no significant difference in overall 17-dihydroexemestane glucuronidation as determined by $V_{max}/K_M$ are observed for the three variant UGT1A4 isoforms, Table 2. The prevalence of the polymorphic UGT2B17 whole-gene deletion is ~30% in Caucasians, Gallagher, C. et al., *Cancer Epidemiol Biomarkers Prev* 2007; 16: 823-8; Wilson, W. et al., *Genomics,* 84: 707-14, 2004; and Gallagher, C. et al., *Free Radic Biol Med,* 46: 20-4, 2009.

Figure 6A:
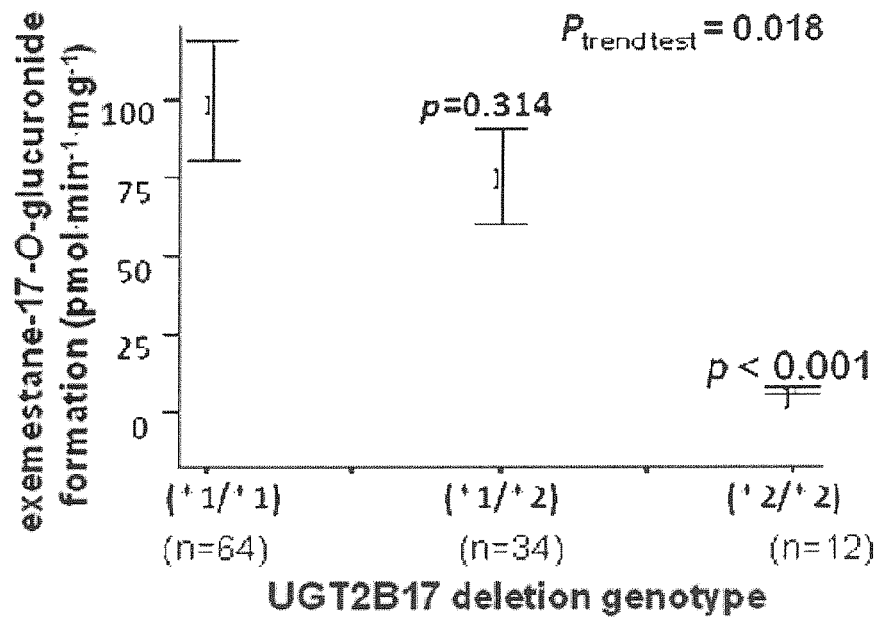
FIG. 6A is a graph showing exesmestane-17-O-glucuronide formation as a function of UGT2B17 genotype.
Figure 6B:
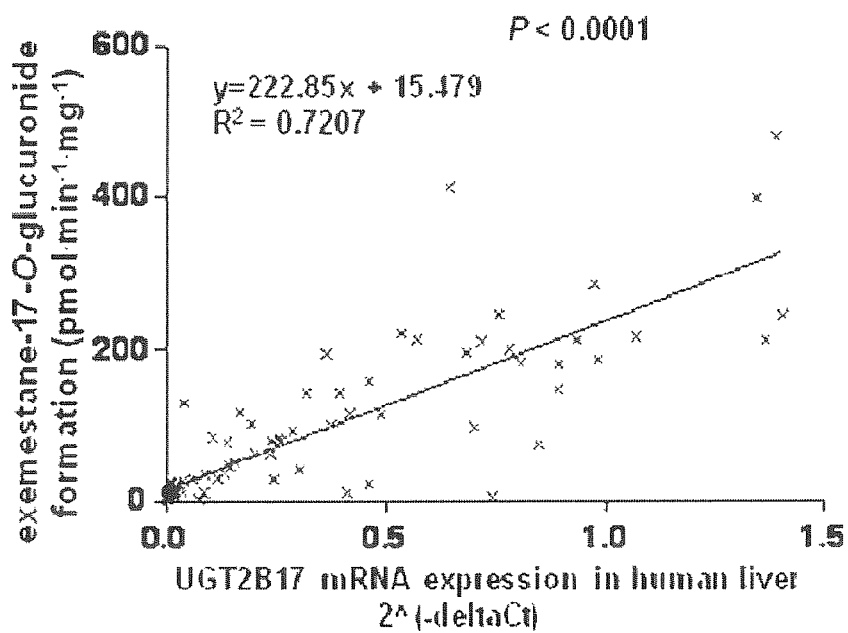
FIG. 6B is a graph showing exesmestane-17-O-glucuronide formation as a function of UGT2B17 mRNA expression in human liver.

To explore a possible relationship between 17-dihydroexemestane glucuronidation and the UGT2B17 deletion, a series of 110 HLM are examined, the rate of exemestane-17-O-glucuronide formation is determined by UPLC using 9.4 μM 17-dihydroexemestane, a concentration that lies within the linear range of kinetic analysis for HLM against 17-dihydroexemestane. As shown in FIGS. 6A-6B, there is a significant (p<0.001) 14-fold decrease in glucuronidation activity against 17-dihydroexemestane in HLM from subjects exhibiting the homozygous UGT2B17 deletion genotype (*2/*2) as compared with HLM from subjects wild type for UGT2B17 (*1/*1), FIG. 6A. There is a significant (p=0.018) trend of decreasing HLM exemestane-17-O-glucuronide formation and increasing numbers of the UGT2B17 deletion allele in the specimens examined. A significant (p<0.0001, R$^2$=0.72) correlation is observed between exemestane-17-O-glucuronide formation in HLM and UGT2B17 expression in the same HLM, FIG. 6B. In addition, HLM from subjects exhibiting the UGT2B17 (*2/*2) genotype exhibited a $K_M$ that is on average 1.7-fold higher (p=0.012), a $V_{max}$ that is on average 22-fold lower (p=0.025), and a $V_{max}/K_M$ that is on average 36-fold lower (p=0.023) than HLM from subjects with the UGT2B17 (*1/*1) genotype, shown in Table 3.

TABLE 3

Kinetic analysis of 17-dihydroexemestane glucuronidation by individual HLM specimens from subjects by UGT2B17 genotype.

| HLM # | UGT2B17 genotype | $V_{max}$ (pmol · min$^{-1}$ · mg$^{-1}$)$^a$ | $K_M$ (μM) | $V_{max}/K_M$ (μl · min$^{-1}$ · mg$^{-1}$)$^a$ |
|---|---|---|---|---|
| 972 | (*1/*1) | 51.6 | 10.6 | 4.9 |
| 1183 | (*1/*1) | 322 | 7.2 | 45 |
| 1392 | (*1/*1) | 393 | 7.1 | 55 |
| 2167 | (*1/*1) | 38.9 | 5.1 | 7.6 |
| 2412 | (*1/*1) | 213 | 6.7 | 32 |
| mean ± S.D. | | 204 ± 158 | 7.3 ± 2.0 | 28.8 ± 22.3 |
| 383 | (*2/*2) | 17.0 | 9.3 | 1.8 |
| 416 | (*2/*2) | 5.6 | 17 | 0.3 |
| 2174 | (*2/*2) | 13.0 | 12.4 | 1.0 |

TABLE 3-continued

Kinetic analysis of 17-dihydroexemestane glucuronidation by
individual HLM specimens from subjects by UGT2B17 genotype.

| HLM # | UGT2B17 genotype | $V_{max}$ (pmol · min$^{-1}$ · mg$^{-1}$)$^a$ | $K_M$ (μM) | $V_{max}/K_M$ (μl · min$^{-1}$ · mg$^{-1}$)$^a$ |
|---|---|---|---|---|
| 2175 | (*2/*2) | 2.3 | 13 | 0.2 |
| 3873 | (*2/*2) | 8.1 | 11 | 0.8 |
| mean ± S.D. | | 9.2 ± 5.9 | 12.8 ± 3.0 | 0.8 ± 0.6 |
| p-value$^b$ | | 0.025 | 0.012 | 0.023 |

$^a$Kinetic data expressed per mg HLM protein.
$^b$Comparing the UGT2B17 (*1/*1) versus (*2/*2) groups.

Example 11

Statistical Analysis

The Student's t-test (2-sided) is used for comparing rates and kinetic values of glucuronide formation for individual UGT1A and UGT2B enzymes and variants against 17-dihydroexemestane. Kinetic data described herein are calculated using $V_{max}$'s that are normalized based on UGT expression in the different active UGT overexpressing cell homogenates, with UGT expression determined by Western blot analysis, Sun, D. et al., *Drug Metab Dispos;* 35: 2006-14, 2007; and Dellinger, R. et al., *Carcinogenesis,* 28: 2412-8, 2007. Aromatase inhibition activity and kinetic constants are determined using Graphpad Prism 5 software. The rate of exemestane-17-O-glucuronide formation in HLM is compared by UGT2B17 gene deletion genotype (homozygotes, heterozygotes and wild type) by trend test and Student's t-test using SPSS statistical software (version 15.0, SPSS, Inc.).

Example 12

Determination of Exesmestane Use by a Subject

A urine sample is obtained from a subject in order to assay for a glucuronidated 17-dihydroexemestane. Presence of glucuronidated 17-Dihydroexemestane is analyzed using a Waters ACQUITY ultra-pressure liquid chromatography (UPLC) System (Milford, Mass.) with a 1.7μ ACQUITY UPLC BEH C18 analytical column (2.1 mm×50 mm, Waters, Ireland) in series with a 0.2 μm Waters assay frit filter (2.1 mm, Waters, USA). The gradient elution conditions, using a flow rate of 0.3 ml/min, are as follows: starting with 19% acetonitrile and 81% buffer A (5 mM ammonium acetate, pH 5.0) for 1 min, a subsequent linear gradient to 75% acetonitrile/25% buffer over 2 min is performed and then maintained at 75% acetonitrile for 2 min.

No detectable exemestane-17-O-glucuronide is present in the urine sample analyzed. A buccal swab sample obtained from the subject is used to isolate genomic DNA from the subject is assayed for a UGT2B17 gene deletion polymorphism. Reactions (20 μl) are performed in 384-well plates using the ABI 7900 HT Sequence Detection System, with incubations at 50° C. for 2 min; 95° C. for 15 min; and 40 cycles of 94° C. for 1 min, 60° C. for 1 min 30 sec. Reactions include QuantiTect Multiplex PCR Master Mix (1× final concentration; Qiagen, Valencia, Calif.), 0.4 μM for each primer (SEQ ID Nos. 1, 2, 4 and 5), 0.2 μM for each probe (SEQ ID No. 3 and 6), and 20-100 ng of DNA. Negative controls (no DNA template) are run on every plate and genotypes are assigned by the automatic calling feature of the allelic discrimination option in SDS 2.2.2 software (Applied Biosystems, Foster City, Calif.).

The UGT2B17 gene deletion polymorphism is detected in the subject, indicating that no functional UGT2B17 is present in the subject and that the negative result of the urine analysis may be a false negative.

A blood sample is obtained from the subject to determine whether exemestane is present in the blood. Plasma is isolated from the blood sample and exemestane assayed in the plasma sample using liquid chromatography with tandem mass spectrometry detection. For this, exemestane is extracted by solid phase extraction. A Waters ACQUITY ultra-pressure liquid chromatography (UPLC) System (Milford, Mass.) with a 1.7μ ACQUITY UPLC BEH C18 analytical column (2.1 mm×50 mm, Waters, Ireland) in series with a 0.2 μm Waters assay frit filter (2.1 mm, Waters, USA) is used for the chromatographic separation. A heated nebulizer interface is used for mass spectrometry, 297→121 m/z for exemestane, operated in positive ion mode. Detection of exemestane in the blood sample indicates that the lack of detection of exemestane-17-O-glucuronide in the urine sample is a false negative due to the UGT2B17 gene deletion polymorphism in the subject.

REFERENCES

Antoniou, T., Tseng, A. L. (2005). Interactions between antiretrovirals and antineoplastic drug therapy. Clin Pharmacokinet 44(2):111-145.

Ariazi E A, Leitao A, Oprea T I, Chen B, Louis T, Bertucci A M, et al. Exemestane's 17-hydroxylated metabolite exerts biological effects as an androgen. Mol Cancer Ther 2007; 6: 2817-27.

Arimidex Anastrozole Tablets. from http://www1.astrazeneca-us.com/pi/arimidex.pdf Aromasin Exemestane Tablets. (2007). from http://www.pfizer.com/files/products/uspi_aromasin.pdf Balliet R M, Chen G, Gallagher C J, Dellinger R W, Sun D, Lazarus P. Characterization of UGTs active against SAHA and association between SAHA glucuronidation activity phenotype with UGT genotype. Cancer Res 2009; 69: 2981-9.

Berkovitz, G. D., Brown, T. R., Fujimoto, M. (1987). Aromatase activity in human skin fibroblasts grown in cell culture. Steroids 50(1-3):281-295.

Bernardi, A., Zamagni, C., Di Fabio, F., al, e. (2002). Randomized comparative study on estrogen suppression induced by 3 different aromatase inhibitors in postmenopausal patients with advanced breast cancer. Program and abstracts of the 38th Annual Meeting of the American Society of Clinical Oncology (May 18-21):217.

Blevins-Primeau, A. S., Sun, D., Chen, G., Sharma, A. K., Gallagher, C. J., Amin, S., et al. (2009). Functional Significance of UDP-Glucuronosyltransferase Variants in the Metabolism of Active Tamoxifen Metabolites. Cancer Res.

Boccardo, F., Rubagotti, A., Puntoni, M., Guglielmini, P., Amoroso, D., Fini, A., et al. (2005). Switching to anastrozole versus continued tamoxifen treatment of early breast cancer: preliminary results of the Italian Tamoxifen Anastrozole Trial. J Clin Oncol 23(22):5138-5147.

Bulun, S. E., Simpson, E. R. (1994). Competitive reverse transcription-polymerase chain reaction analysis indicates that levels of aromatase cytochrome P450 transcripts in adipose tissue of buttocks, thighs, and abdomen of women increase with advancing age. J Clin Endocrinol Metab 78(2): 428-432.

Buzdar, A. U., Guastalla, J. P., Nabholtz, J. M., Cuzick, J., Group, A. T. (2006). Impact of chemotherapy regimens prior to endocrine therapy: Results from the ATAC (Anastrozole and Tamoxifen, Alone or in Combination) trial. Cancer 107(3):472-480.

Buzdar, A. U., Jonat, W., Howell, A., Jones, S. E., Blomqvist, C. P., Vogel, C. L., et al. (1998). Anastrozole versus megestrol acetate in the treatment of postmenopausal women with advanced breast carcinoma: results of a survival update based on a combined analysis of data from two mature phase III trials. Arimidex Study Group. Cancer 83(6):1142-1152.

Buzdar, A. U., Jones, S. E., Vogel, C. L., Wolter, J., Plourde, P., Webster, A. (1997). A phase III trial comparing anastrozole (1 and 10 milligrams), a potent and selective aromatase inhibitor, with megestrol acetate in postmenopausal women with advanced breast carcinoma. Arimidex Study Group. Cancer 79(4):730-739.

Buzzetti, F., Di Salle, E., Longo, A., Briatico, G. (1993). Synthesis and aromatase inhibition by potential metabolites of exemestane (6-methylenandrosta-1,4-diene-3,17-dione). Steroids 58(11):527-532.

Coates, A. S., Keshaviah, A., Thurlimann, B., Mouridsen, H., Mauriac, L., Forbes, J. F., et al. (2007). Five years of letrozole compared with tamoxifen as initial adjuvant therapy for postmenopausal women with endocrine-responsive early breast cancer: update of study BIG 1-98. J Clin Oncol 25(5): 486-492.

Coleman, R. E., Banks, L. M., Girgis, S. I., Kilburn, L. S., Vrdoljak, E., Fox, J., et al. (2007). Skeletal effects of exemestane on bone-mineral density, bone biomarkers, and fracture incidence in postmenopausal women with early breast cancer participating in the Intergroup Exemestane Study (IES): a randomised controlled study. Lancet Oncol 8(2):119-127.

Coombes, R. C., Kilburn, L. S., Snowdon, C. F., Paridaens, R., Coleman, R. E., Jones, S. E., et al. (2007). Survival and safety of exemestane versus tamoxifen after 2-3 years' tamoxifen treatment (Intergroup Exemestane Study): a randomised controlled trial. Lancet 369(9561):559-570.

Coughtrie M W, Burchell B, Bend J R. A general assay for UDPglucuronosyltransferase activity using polar amino-cyano stationary phase HPLC and UDP[U-14C]glucuronic acid. Anal Biochem 1986; 159: 198-205.

Deeks E D, Scott L J. Exemestane: a review of its use in postmenopausal women with breast cancer. Drugs 2009; 69: 889-918.

di Salle E, Ornati, G., Paridaens, R., Coombes, R. C., Lobelle, J. P., Zurlo, M. G. Preclinical and clinical pharmacology of the aromatase inhibitor exemestane (FCE24304). In: Motta M, Serio, M., editor. Sex Hormones and Antihormones in Endocrine Dependent Pathology: Basic and Clinical Aspects. Amsterdam: Elsevier; 1994. p. 279-86.

Dombernowsky, P., Smith, I., Falkson, G., Leonard, R., Panasci, L., Bellmunt, J., et al. (1998). Letrozole, a new oral aromatase inhibitor for advanced breast cancer: double-blind randomized trial showing a dose effect and improved efficacy and tolerability compared with megestrol acetate. J Clin Oncol 16(2):453-461.

Dowsett, M., Cuzick, J., Howell, A., Jackson, I. (2001). Pharmacokinetics of anastrozole and tamoxifen alone, and in combination, during adjuvant endocrine therapy for early breast cancer in postmenopausal women: a sub-protocol of the 'Arimidex and tamoxifen alone or in combination' (ATAC) trial. Br J Cancer 85(3):317-324.

Eisen, A., Trudeau, M., Shelley, W., Messersmith, H., Pritchard, K. I. (2008). Aromatase inhibitors in adjuvant therapy for hormone receptor positive breast cancer: a systematic review. Cancer Treat Rev 34(2):157-174.

Evans T R, Di Salle E, Ornati G, Lassus M, Benedetti M S, Pianezzola E, et al. Phase I and endocrine study of exemestane (FCE 24304), a new aromatase inhibitor, in postmenopausal women. Cancer Res 1992; 52: 5933-9.

Exemestane for advanced breast cancer. (2000). Med Lett Drugs Ther 42(1076):35-36.

Femara. (2004). from http://www.fda.gov/cder/foi/label/2004/020726s0111b1.pdf

Ferretti, G., Bria, E., Giannarelli, D., Felici, A., Papaldo, P., Fabi, A., et al. (2006). Second- and third-generation aromatase inhibitors as first-line endocrine therapy in postmenopausal metastatic breast cancer patients: a pooled analysis of the randomised trials. Br J Cancer 94(12):1789-1796.

Forbes, J. F., Cuzick, J., Buzdar, A., Howell, A., Tobias, J. S., Baum, M. (2008). Effect of anastrozole and tamoxifen as adjuvant treatment for early-stage breast cancer: 100-month analysis of the ATAC trial. Lancet Oncol 9(1):45-53.

Gallagher, C. J., Muscat, J. E., Hicks, A. N., Zheng, Y., Dyer, A. M., Chase, G. A., et al. (2007). The UDP-glucuronosyltransferase 2B17 gene deletion polymorphism: sex-specific association with urinary 4-(methylnitrosamino)-1-(3-pyridyl)-1-butanol glucuronidation phenotype and risk for lung cancer. Cancer Epidemiol Biomarkers Prey 16(4):823-828.

Geisler, J., Haynes, B., Anker, G., Dowsett, M., Lonning, P. E. (2002). Influence of letrozole and anastrozole on total body aromatization and plasma estrogen levels in postmenopausal breast cancer patients evaluated in a randomized, cross-over study. J Clin Oncol 20(3):751-757, Grana G. Adjuvant aromatase inhibitor therapy for early breast cancer: A review of the most recent data. J Surg Oncol 2006; 93: 585-92.

Howell, A., Cuzick, J., Baum, M., Buzdar, A., Dowsett, M., Forbes, J. F., et al. (2005). Results of the ATAC (Arimidex, Tamoxifen, Alone or in Combination) trial after completion of 5 years' adjuvant treatment for breast cancer. Lancet 365 (9453):60-62.

Howell, A., Group, A. T. (2006). Analysis of fracture risk factors from the 'Arimadex' Tamoxifen, Alone or in Combination (ATAC) trial: 5-year data [abstract]. J Clin Oncol 24:A563.

Hozumi, Y., Suemasu, K., Takehara, M., Takei, H., Aihara, T., Tamura, M. (2006). The effect of exemestane, anastrozole and tamoxifen on the lipidemic profile of postmeonpausal early breast cancer patients: preliminary results of NSAS (national surgical adjusvant study). Breast Cancer Res Treat 100:A4051.

Karaer O, Oruc S, Koyuncu F M. Aromatase inhibitors: possible future applications. Acta Obstet Gynecol Scand 2004; 83: 699-706.

Kaufmann, M., Bajetta, E., Dirix, L. Y., Fein, L. E., Jones, S. E., Zilembo, N., et al. (2000). Exemestane is superior to megestrol acetate after tamoxifen failure in postmenopausal women with advanced breast cancer: results of a phase III randomized double-blind trial. The Exemestane Study Group. J Clin Oncol 18(7):1399-1411.

Lonning P E. Pharmacological profiles of exemestane and formestane, steroidal aromatase inhibitors used for treatment of postmenopausal breast cancer. Breast Cancer Res Treat 1998; 49 Suppl 1: S45-52; discussion S73-7.

Mareck, U., Geyer, H., Guddat, S., Haenelt, N., Koch, A., Kohler, M., et al. (2006). Identification of the aromatase inhibitors anastrozole and exemestane in human urine using liquid chromatography/tandem mass spectrometry. Rapid Commun Mass Spectrom 20(12):1954-1962.

Markopoulos, C., Polychronis, A., Zobolas, V., Xepapadakis, G., Papadiamantis, J., Koukouras, D., et al. (2005).

The effect of exemestane on the lipidemic profile of postmenopausal early breast cancer patients: preliminary results of the TEAM Greek sub-study. Breast Cancer Res Treat 93(1):61-66.

Matsumine, H., Hirato, K., Yanaihara, T., Tamada, T., Yoshida, M. (1986). Aromatization by skeletal muscle. J Clin Endocrinol Metab 63(3):717-720.

McCarroll, S. A., Hadnott, T. N., Perry, G. H., Sabeti, P. C., Zody, M. C., Barrett, J. C., et al. (2006). Common deletion polymorphisms in the human genome. Nat Genet 38(1):86-92.

Means, G. D., Kilgore, M. W., Mahendroo, M. S., Mendelson, C. R., Simpson, E. R. (1991). Tissue-specific promoters regulate aromatase cytochrome P450 gene expression in human ovary and fetal tissues. Mol Endocrinol 5(12):2005-2013.

Murata, M., Warren, E. H., Riddell, S. R. (2003). A human minor histocompatibility antigen resulting from differential expression due to a gene deletion. J Exp Med 197(10):1279-1289.

Nakamura, A., Nakajima, M., Yamanaka, H., Fujiwara, R., Yokoi, T. (2008). Expression of UGT1A and UGT2B mRNA in human normal tissues and various cell lines. Drug Metab Dispos 36(8):1461-1464.

Nelson, L. R., Bulun, S. E. (2001). Estrogen production and action. J Am Acad Dermatol 45(3 Suppl):S116-124.

Perez, E. A., Josse, R. G., Pritchard, K. I., Ingle, J. N., Martino, S., Findlay, B. P., et al. (2006). Effect of letrozole versus placebo on bone mineral density in women with primary breast cancer completing 5 or more years of adjuvant tamoxifen: a companion study to NCIC CTG MA.17. J Clin Oncol 24(22):3629-3635.

Ren, Q., Murphy, S. E., Zheng, Z., Lazarus, P. (2000). O-Glucuronidation of the lung carcinogen 4-(methylnitrosamino)-1-(3-pyridyl)-1-butanol (NNAL) by human UDP-glucuronosyltransferases 2B7 and 1A9. Drug Metab Dispos 28(11):1352-1360.

Roselli, C. E., Horton, L. E., Resko, J. A. (1985). Distribution and regulation of aromatase activity in the rat hypothalamus and limbic system. Endocrinology 117(6):2471-2477.

Shozu, M., Simpson, E. R. (1998). Aromatase expression of human osteoblast-like cells. Mol Cell Endocrinol 139(1-2):117-129.

Sioufi, A., Gauducheau, N., Pineau, V., Marfil, F., Jaouen, A., Cardot, J. M., et al. (1997). Absolute bioavailability of letrozole in healthy postmenopausal women. Biopharm Drug Dispos 18(9):779-789.

Strassburg, C. P., Strassburg, A., Nguyen, N., Li, Q., Manns, M. P., Tukey, R. H. (1999). Regulation and function of family 1 and family 2 UDP-glucuronosyltransferase genes (UGT1A, UGT2B) in human oesophagus. Biochem J 338 (Pt 2):489-498.

Sun D, Sharma A K, Dellinger R W, Blevins-Primeau A S, Balliet R M, Chen G, et al. Glucuronidation of active tamoxifen metabolites by the human UDP glucuronosyltransferases. Drug Metab Dispos 2007; 35: 2006-14.

Thurlimann, B., Keshaviah, A., Coates, A. S., Mouridsen, H., Mauriac, L., Forbes, J. F., et al. (2005). A comparison of letrozole and tamoxifen in postmenopausal women with early breast cancer. N Engl J Med 353(26):2747-2757.

Traina T A, Poggesi I, Robson M, Asnis A, Duncan B A, Heerdt A, et al. Pharmacokinetics and tolerability of exemestane in combination with raloxifene in postmenopausal women with a history of breast cancer. Breast Cancer Res Treat 2008; 111: 377-88.

Tsai-Morris, C. H., Aquilano, D. R., Dufau, M. L. (1985). Cellular localization of rat testicular aromatase activity during development. Endocrinology 116(1):38-46.

Turgeon, D., Carrier, J. S., Levesque, E., Hum, D. W., Belanger, A. (2001). Relative enzymatic activity, protein stability, and tissue distribution of human steroid-metabolizing UGT2B subfamily members. Endocrinology 142(2):778-787.

Wiener, D., Fang, J. L., Dossett, N., Lazarus, P. (2004). Correlation between UDP-glucuronosyltransferase genotypes and 4-(methylnitrosamino)-1-(3-pyridyl)-1-butanone glucuronidation phenotype in human liver microsomes. Cancer Res 64(3):1190-1196.

Wilson, W., 3rd, Pardo-Manuel de Villena, F., Lyn-Cook, B. D., Chatterjee, P. K., Bell, T. A., Detwiler, D. A., et al. (2004). Characterization of a common deletion polymorphism of the UGT2B17 gene linked to UGT2B15. Genomics 84(4):707-714.

Zheng, Z., Fang, J. L., Lazarus, P. (2002). Glucuronidation: an important mechanism for detoxification of benzo[a]pyrene metabolites in aerodigestive tract tissues. Drug Metab Dispos 30(4): 397-403.

Fang J L, Beland F A, Doerge D R, Wiener D, Guillemette C, Marques M M, et al. Characterization of benzo(a)pyrene-trans-7,8-dihydrodiol glucuronidation by human tissue microsomes and overexpressed UDP-glucuronosyltransferase enzymes. Cancer Res 2002; 62: 1978-86.

Dellinger R W, Chen G, Blevins-Primeau A S, Krzeminski J, Amin S, Lazarus P. Glucuronidation of PhIP and N—OH-PhIP by UDP-glucuronosyltransferase 1A10. Carcinogenesis 2007; 28: 2412-8.33.

Izukawa T, Nakajima M, Fujiwara R, Yamanaka H, Fukami T, Takamiya M, et al. Quantitative analysis of UDP-glucuronosyltransferase (UGT) 1A and UGT2B expression levels in human livers. Drug Metab Dispos 2009; 37: 1759-68.

Itaaho K, Court M H, Uutela P, Kostiainen R, Radominska-Pandya A, Finel M. Dopamine is a low-affinity and high-specificity substrate for the human UDPglucuronosyltransferase 1A10. Drug Metab Dispos 2009; 37: 768-75.

Lazarus P, Sun D. Potential role of UGT pharmacogenetics in cancer treatment and prevention: focus on tamoxifen and aromatase inhibitors. Drug Metab Rev; 42: 176-88.

Dellinger R W, Fang J L, Chen G, Weinberg R, Lazarus P. Importance of udpglucuronosyltransferase 1a10 (ugt1a10) in the detoxification of polycyclic aromatic hydrocarbons: decreased glucuronidative activity of the ugt1a10139lys isoform. Drug Metab Dispos 2006; 34: 943-9.

Gallagher C J, Ahn K, Knipe A L, Dyer A M, Richie J P, Jr., Lazarus P, et al. Association between haplotypes of manganese superoxide dismutase (SOD2), smoking, and lung cancer risk. Free Radic Biol Med 2009; 46: 20-4.

Jannuzzo M G, Poggesi I, Spinelli R, Rocchetti M, Cicioni P, Buchan P. The effects of degree of hepatic or renal impairment on the pharmacokinetics of exemestane in postmenopausal women. Cancer Chemother Pharmacol 2004; 53: 475-81.

Strassburg C P, Oldhafer K, Manns M P, Tukey R H. Differential expression of the UGT1A locus in human liver, biliary, and gastric tissue: identification of UGT1A7 and UGT1A10 transcripts in extrahepatic tissue. Mol Pharmacol 1997; 52: 212-20.

Strassburg C P, Manns M P, Tukey R H. Expression of the UDPglucuronosyltransferase 1A locus in human colon. Identification and characterization of the novel extrahepatic UGT1A8. J Biol Chem 1998; 273: 8719-26.

Lehmann L, Wagner J. Gene expression of 17beta-estradiol-metabolizing isozymes: comparison of normal human mammary gland to normal human liver and to cultured human breast adenocarcinoma cells. Adv Exp Med Biol 2008; 617: 617-24.

Starlard-Davenport A, Lyn-Cook B, Radominska-Pandya A. Identification of UDPglucuronosyltransferase 1A10 in non-malignant and malignant human breast tissues. Steroids 2008; 73: 611-20.

Lazarus P, Zheng Y, Aaron Runkle E, Muscat J E, Wiener D. Genotype/phenotype correlation between the polymorphic UGT2B17 gene deletion and NNAL glucuronidation activities in human liver microsomes. Pharmacogenet Genomics 2005; 15: 769-78.

Chen G, Blevins-Primeau A S, Dellinger R W, Muscat J E, Lazarus P. Glucuronidation of nicotine and cotinine by UGT2B10: loss of function by the UGT2B10 Codon 67 (Asp>Tyr) polymorphism. Cancer Res 2007; 67: 9024-9.

Corona G, Elia C, Casetta B, Diana C, Rosalen S, Bari M, et al. A liquid chromatography-tandem mass spectrometry method for the simultaneous determination of exemestane and its metabolite 17-dihydroexemestane in human plasma. J Mass Spectrom 2009; 44: 920-8.

*Homo sapiens* UDP-glucuronosyltransferase 2B17 precursor; Mature protein is 25-530; signal peptide is 1-24; SEQ ID No. 7

```
  1 mslkwmsvfl lmqlscyfss gscgkvlvwp teyshwinmk tileelvqrg hevivltssa
 61 silvnaskss aiklevypts ltkndledff mkmfdrwtys iskntfwsyf sqlqelcwey
121 sdyniklced avlnkklmrk lqeskfdvll adavnpcgel laellnipfl yslrfsvgyt
181 veknggglf  ppsyvpvvms elsdqmifme riknmiymly fdfwfqaydl kkwdqfysev
241 lgrpttlfet mgkaemwlir tywdfefprp flpnvdfvgg lhckpakplp kemeefvqss
301 gengivvfsl gsmisnmsee sanmiasala qipqkvlwrf dgkkpntlgs ntrlykwlpq
361 ndllghpktk afithggtng iyeaiyhgip mvgiplfadq hdniahmkak gaalsvdirt
421 mssrdllnal ksvindpiyk enimklsrih hdqpvkpldr avfwiefvmr hkgakhlrva
481 ahnltwiqyh sldviaflla cvatmifmit kcclfcfrkl aktgkkkkrd
```

Nucleic acid sequence encoding *Homo sapiens* UDP-glucuronosyltransferase 2B17 precursor; SEQ ID No. 8

```
   1 atgtctctga aatggatgtc agtctttctg ctgatgcagc tcagttgtta ctttagctct
  61 gggagttgtg gaaaggtgct ggtgtggccc acagaataca gccattggat aaatatgaag
 121 acaatcctgg aagagcttgt tcagagggt  catgaggtga ttgtgttgac atcttcggct
 181 tctattcttg tcaatgccag taaatcatct gctattaaat tagaagttta tcctacatct
 241 ttaactaaaa atgatttgga agatttttt  atgaaaatgt tcgatagatg gacatatagt
 301 atttcaaaaa atacattttg gtcatatttt tcacaactac aagaattgtg ttgggaatat
 361 tctgactata atataaagct ctgtgaagat gcagttttga acaagaaact tatgagaaaa
 421 ctacaagagt caaaatttga tgtccttctg gcagatgccg ttaatccctg tggtgagctg
 481 ctggctgagc tacttaacat accctttctg tacagtctcc gcttctctgt tggctacaca
 541 gttgagaaga atggtggagg atttctgttc cctccttcct atgtacctgt tgttatgtca
 601 gaattaagtg atcaaatgat tttcatggag aggataaaaa atatgatata tatgctttat
 661 tttgactttt ggtttcaagc atatgatctg aagaagtggg accagtttta tagtgaagtt
 721 ctaggaagac ccactacatt atttgagaca atggggaaag ctgaaatgtg gctcattcga
 781 acctattggg attttgaatt tcctcgccca ttcttaccaa atgttgattt tgttggagga
 841 cttcactgta aaccagccaa accttgcct  aaggaaatgg aagagtttgt gcagagctct
 901 ggagaaaatg gtattgtggt gttttctctg ggtcgatga  tcagtaacat gtcagaagaa
 961 agtgccaaca tgattgcatc agcccttgcc cagatccac  aaaaggttct atggagattt
1021 gatggcaaga agccaaatac tttaggttcc aatactcgac tgtataagtg gttaccccag
1081 aatgaccttc ttggtcatcc caaaaccaaa gcttttataa ctcatggtgg aaccaatggc
1141 atctatgagg caatctacca tggatccct  atggtgggca ttcccttgtt tgcggatcaa
1201 catgataaca ttgctcacat gaaagccaag ggagcagccc tcagtgtgga catcaggacc
```

```
-continued
1261 atgtcaagta gagatttgct caatgcattg aagtcagtca ttaatgaccc tatctataaa 1321 gagaatatca tgaaattatc aagaattcat catgatcaac cggtgaagcc cctggatcga 1381 gcagtcttct ggattgagtt tgtcatgcgc cataaaggag ccaagcacct tcgggtcgca 1441 gcccacaacc tcacctggat ccagtaccac tctttggatg tgatagcatt cctgctggcc 1501 tgcgtggcaa ctatgatatt tatgatcaca aaatgttgcc tgttttgttt ccgaaagctt 1561 gccaaaacag gaaagaagaa gaaaagggat tag
```

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

---

The invention claimed is:

1. A method for aiding in determining therapeutic efficacy of exesmestane in a subject who has or is at risk of having a condition or disease for which inhibition of aromatase is desirable to decrease estrogen in the subject, comprising:
   assaying a biological sample obtained from the subject for a UDP glucuronosyltransferase 2 family, polypeptide B17 gene deletion polymorphism, wherein detection of the UDP glucuronosyltransferase 2 family, polypeptide B17gene deletion polymorphism is correlated with altered therapeutic efficacy of the exesmestane in the subject compared to a control subject; and
   treating the subject with exemestane based on a result of assaying the biological sample where the subject is determined to have no UDP glucuronosyltransferase 2 family, polypeptide B17 gene deletion polymorphism or determining an alternative treatment without exemestane based on a result of assaying the biological sample where the subject is determined to have a UDP glucuronosyltransferase 2 family, polypeptide B17 gene deletion polymorphism.

2. The method of claim 1, wherein the assaying comprises polymerase chain reaction.

3. The method of claim 2 wherein the polymerase chain reaction is a real-time polymerase chain reaction.

4. The method of claim 1 wherein the subject is human.

5. The method of claim 1, wherein the sample comprises genomic DNA.

6. The method of claim 1, wherein the assaying comprises hybridization of nucleic acids in the sample with a probe specific for the UDP glucuronosyltransferase 2 family, polypeptide B17 gene under suitable hybridization conditions, and detection of hybridization of the probe and the nucleic acids, wherein a lack of detectable hybridization of the probe and the nucleic acids is indicative of a UDP glucuronosyltransferase 2 family, polypeptide B17 gene deletion polymorphism correlated with altered therapeutic efficacy of the exesmestane in the subject compared to a control subject.

7. A kit for aiding in determining therapeutic efficacy of exemestane in a subject, comprising:
   at least one reagent for detection of a UDP glucuronosyltransferase 2 family, polypeptide B17 gene deletion polymorphism in a sample obtained from the subject; and
   at least one reagent for detecting aromatase in the sample obtained from the subject.

8. The kit of claim 7 wherein the kit comprises at least one reagent for detection of a UDP glucuronosyltransferase 2 family, polypeptide B17 gene deletion polymorphism nucleic acid or protein.

9. The kit of claim 7 wherein the kit comprises at least one reagent for detection of a UDP glucuronosyltransferase 2 family, polypeptide B17 gene deletion polymorphism protein.

10. The kit of claim 7 wherein the at least one reagent for detecting aromatase comprises a first primer comprising the nucleotide sequence of SEQ ID NO:9 and a second primer comprising the nucleotide sequence of SEQ ID NO:10.

11. A method of detecting exesmestane use in a subject, comprising:
   assaying a biological sample obtained from the subject for a UDP glucuronosyltransferase 2 family, polypeptide B17 gene deletion polymorphism, wherein detection of the UDP glucuronosyltransferase 2 family, polypeptide B17 gene deletion polymorphism is correlated with decreased production of glucuronidated 17-dihydroexemestane in the urine of the subject, wherein detecting no UDP glucuronosyltransferase 2 family, polypeptide B17 gene deletion polymorphism supports a finding of no exemestane use in the subject when glucuronidated 17-dihydroexemestane is not detected in urine; and
   assaying a blood sample obtained from the subject for exemestane where the assaying detects a UDP glucuronosyltransferase 2 family, polypeptide B17 gene deletion polymorphism.

12. A method for aiding in determining therapeutic efficacy of an aromatase inhibitor in a subject who has or is at risk of having a condition or disease for which inhibition of aromatase is desirable to decrease estrogen in the subject, comprising:
   detecting expression and/or function of at least one UDP-glucuronosyltransferase having activity to modify at least one aromatase inhibitor and/or metabolite of the aromatase inhibitor by glucuronidation, wherein detection of expression and/or function of the UDP-glucuronosyltransferase is correlated with therapeutic efficacy of the aromatase inhibitor in the subject; and
   selecting a treatment for the subject based on detecting expression and/or function of at least one UDP-glucuronosyltransferase having activity to modify at least one aromatase inhibitor and/or metabolite of the aromatase inhibitor by glucuronidation.

13. The method of claim 12, wherein the UDP-glucuronosyltransferase is UDP glucuronosyltransferase 2 family, polypeptide B17 (UGT2B17) and the aromatase inhibitor is exemestane.

14. The method of claim 12, wherein detection of UDP-glucuronosyltransferase expression and/or function comprises detection of a UDP-glucuronosyltransferase gene deletion polymorphism in the subject.

15. The method of claim 14, wherein the deletion polymorphism is a UGT2B17 gene deletion polymorphism.

16. The method of claim 14 wherein the detecting comprises polymerase chain reaction.

17. The method of claim 12 wherein the subject is human.

18. The method of claim 12 wherein the detecting comprises contacting a subject sample and a UDP-glucuronosyltransferase binding moiety selected from the group consisting of: an antibody and an aptamer.

* * * * *

UNITED STATES PATENT AND TRADEMARK OFFICE
CERTIFICATE OF CORRECTION

| | | |
|---|---|---|
| PATENT NO. | : 8,476,023 B2 | Page 1 of 1 |
| APPLICATION NO. | : 12/852957 | |
| DATED | : July 2, 2013 | |
| INVENTOR(S) | : Lazarus et al. | |

It is certified that error appears in the above-identified patent and that said Letters Patent is hereby corrected as shown below:

In the Specification:

Column 4, line 42, Delete "Prey.,", Insert -- Prev., --

Column 8, line 49, Delete "tee ruination", Insert -- termination --

Column 10, line 33, Delete "the) (BLAST", Insert -- the XBLAST --

In the Claims:

Column 37, line 10, claim 1, Delete "B17gene", Insert -- B17 gene --

Signed and Sealed this
Nineteenth Day of May, 2015

Michelle K. Lee
*Director of the United States Patent and Trademark Office*